(12) United States Patent
McAllister et al.

(10) Patent No.: US 11,724,079 B2
(45) Date of Patent: Aug. 15, 2023

(54) MICRONEEDLES AND METHODS OF MANUFACTURE THEREOF

(71) Applicant: Georgia Tech Research Corporation, Atlanta, GA (US)

(72) Inventors: Devin McAllister, Marietta, GA (US); Mark R. Prausnitz, Atlanta, GA (US); Sebastien Henry, Smyrna, GA (US); Xin Dong Guo, Atlanta, GA (US)

(73) Assignee: Georgia Tech Research Corporation, Altanta, GA (US)

( * ) Notice: Subject to any disclaimer, the term of this patent is extended or adjusted under 35 U.S.C. 154(b) by 476 days.

(21) Appl. No.: 17/061,203

(22) Filed: Oct. 1, 2020

(65) Prior Publication Data

US 2021/0016071 A1    Jan. 21, 2021

Related U.S. Application Data

(62) Division of application No. 15/306,152, filed as application No. PCT/US2015/027672 on Apr. 24, 2015, now Pat. No. 10,828,478.

(Continued)

(51) Int. Cl.
*A61M 37/00* (2006.01)

(52) U.S. Cl.
CPC . *A61M 37/0015* (2013.01); *A61M 2037/0023* (2013.01); *A61M 2037/0046* (2013.01); *A61M 2037/0053* (2013.01)

(58) Field of Classification Search
CPC ...... A61M 37/0015; A61M 2037/0023; A61M 2037/0046; A61M 2037/0053; A61M 5/3295; A61K 9/0021; B81C 1/00111
See application file for complete search history.

(56) References Cited

U.S. PATENT DOCUMENTS

| 4,097,943 A | 7/1978 | O'Connell |
| 6,007,836 A | 12/1999 | Denzer |

(Continued)

FOREIGN PATENT DOCUMENTS

| CN | 103203072 A | 7/2013 |
| JP | 2007/089792 A | 4/2007 |

(Continued)

OTHER PUBLICATIONS

Extended European Search Report issued in Application No. 15783359.1, dated Nov. 27, 2017 (8 pages).

(Continued)

*Primary Examiner* — Nathan R Price
*Assistant Examiner* — Justin L Zamory
(74) *Attorney, Agent, or Firm* — Eversheds Sutherland (US) LLP

(57) ABSTRACT

A microneedle array is provided for administrating a drug or other substance into a biological tissue. The array includes a base substrate; a primary funnel portion extending from one side of the base substrate; and two or more solid microneedles extending from the primary funnel portion, wherein the two or more microneedles comprise the substance of interest. Methods for making an array of microneedles are also provided. The method may include providing a non-porous and gas-permeable mold having a two or more cavities each of which defines a microneedle; filling the cavities with a fluid material which includes a substance of interest and a liquid vehicle; drying the fluid material to remove at least a portion of the liquid vehicle and form a plurality of microneedles that include the substance of interest, wherein the filling is conducted with a pressure differential applied between opposed surfaces of the mold.

20 Claims, 12 Drawing Sheets

Related U.S. Application Data

(60) Provisional application No. 61/983,593, filed on Apr. 24, 2014.

(56) References Cited

U.S. PATENT DOCUMENTS

| | | |
|---|---|---|
| 6,334,856 B1 | 1/2002 | Allen et al. |
| 6,503,231 B1 | 1/2003 | Prausnitz et al. |
| 6,611,707 B1 | 8/2003 | Prausnitz et al. |
| 6,611,717 B1 | 8/2003 | Clark et al. |
| 6,656,147 B1 | 12/2003 | Gertsek et al. |
| 6,743,211 B1 | 6/2004 | Prausnitz et al. |
| 6,945,952 B2 | 9/2005 | Kwon |
| 7,182,747 B2 | 2/2007 | Kwon |
| 7,211,062 B2 | 5/2007 | Kwon |
| 7,226,439 B2 | 6/2007 | Prausnitz et al. |
| 7,516,845 B2 | 4/2009 | Lang et al. |
| 7,918,814 B2 | 4/2011 | Prausnitz et al. |
| 8,062,573 B2 | 11/2011 | Kwon |
| 8,101,114 B2 | 1/2012 | Park et al. |
| 8,257,324 B2 | 9/2012 | Prausnitz et al. |
| 8,419,708 B2 | 4/2013 | Tokumoto et al. |
| 8,808,225 B2 | 8/2014 | Prausnitz et al. |
| 9,302,903 B2 | 4/2016 | Park et al. |
| 9,364,426 B2 | 6/2016 | Gill et al. |
| 2002/0192273 A1 | 12/2002 | Buseman et al. |
| 2003/0187394 A1 | 10/2003 | Wilkinson et al. |
| 2005/0228340 A1 | 10/2005 | Cleary et al. |
| 2006/0084942 A1 | 4/2006 | Kim et al. |
| 2007/0088248 A1 | 4/2007 | Glenn et al. |
| 2008/0108958 A1 | 5/2008 | Carter et al. |
| 2008/0114298 A1 | 5/2008 | Cantor et al. |
| 2008/0183144 A1 | 7/2008 | Trautman et al. |
| 2009/0118662 A1 | 5/2009 | Schnall |
| 2010/0256568 A1 | 10/2010 | Frederickson et al. |
| 2010/0262081 A1 | 10/2010 | Lee et al. |
| 2011/0152792 A1 | 6/2011 | Takada |
| 2011/0245728 A1 | 10/2011 | Eppstein et al. |
| 2012/0041337 A1 | 1/2012 | Ferguson et al. |
| 2012/0027810 A1 | 2/2012 | Chen et al. |
| 2012/0078189 A1 | 3/2012 | Ogawa et al. |
| 2012/0109065 A1 | 5/2012 | Backes |
| 2012/0283695 A1* | 11/2012 | Chen .................. A61K 31/7088 977/773 |
| 2013/0006187 A1 | 1/2013 | Kobayashi et al. |
| 2013/0023749 A1 | 1/2013 | Afanasweicz et al. |
| 2013/0072874 A1 | 3/2013 | Tokumoto et al. |
| 2013/0158482 A1 | 6/2013 | Davis et al. |
| 2014/0005606 A1* | 1/2014 | Chen .................. A61K 9/5036 604/173 |
| 2016/0213908 A1 | 7/2016 | McAllister et al. |

FOREIGN PATENT DOCUMENTS

| | | |
|---|---|---|
| JP | 2009/039171 A | 2/2009 |
| JP | 2009240410 A | 10/2009 |
| JP | 2012-196426 A | 10/2012 |
| JP | 2013-074924 A | 4/2013 |
| KR | 10-0682534 | 2/2007 |
| WO | 2010/140760 A2 | 12/2010 |
| WO | 2013/096026 A1 | 6/2013 |

OTHER PUBLICATIONS

International Search Report and Written Opinion mailed for PCT/US2015/027672, dated Jul. 23, 2015 (13 pages).

* cited by examiner

MICRONEEDLES AND METHODS OF MANUFACTURE THEREOF

CROSS REFERENCE TO RELATED APPLICATIONS

This application is a divisional of U.S. application Ser. No. 15/306, filed Oct. 24, 2016, which is the U.S. national stage of PCT/US15/27672, filed Apr. 24, 2015, which claims priority to U.S. Provisional Patent Application No. 61/983, 593, filed Apr. 24, 2014, all of which are incorporated herein by reference.

STATEMENT REGARDING FEDERALLY SPONSORED RESEARCH OR DEVELOPMENT

This invention was made with government support under grant number EB012495 awarded by the National Institutes of Health. The government has certain rights in the invention.

BACKGROUND

The present application is generally in the field of microneedle for the transport of therapeutic, diagnostic, cosmetic, biological or other molecules into, out of or across the skin or other tissue barriers.

Microneedles are small in size, which allows them to precisely target superficial tissue layers (e.g., skin) and to be relatively pain free in doing so. However, their small size may hinder other factors that are important for their functionality and/or manufacture. This is particularly true in the case of producing a microneedle patch for transdermal drug delivery.

For example, since microneedles are short in length in comparison to the base or backing from which they are formed or affixed to, tissue insertion can be difficult. This results from the elastic nature of the targeted tissue (e.g., skin) because much of the applied force when administering them to skin is used to deform the skin underneath the entirety of the microneedle patch in order for the microneedles to sufficiently contact and penetrate the tissue. Therefore, the patch application force required for successful microneedle insertion can be higher than the force to insert the microneedles alone. This has resulted in the development of complex and aggressive applicators that apply microneedle patches to the skin with impact. This adds cost and complexity, which are undesirable.

Conventional molding methods generally are not well suited for making microneedle arrays in a simple, fast, highly reproducible and accurate manner. For example, the small size of the microneedles limits the amount of material that can be loaded into them during manufacturing (in the case of delivery) or that can be sampled/extracted in the case of analyte sampling/monitoring. The microneedles have a limited volume, which is similar to the mold cavities from which they are manufactured. This limits the amount of material that can be loaded into them. Making this more challenging is the fact that many molecules of interest have limited solubility in water (one of the preferred carrier solvents during manufacturing) and other solvents.

Manufacturing of small solid microneedles also may suffer from inaccuracies arising from use of conventional fluid dispensing systems and conventional molds. The inaccuracies may stem from misalignment between deposited drops to microneedle cavities and highly variable fill volumes. The small size of the microneedle mold cavities makes them difficult to target with direct deposition technologies especially during high-volume manufacturing. The targeted deposition area is defined by the opening of a microneedle cavity in the mold, which is very small. The volume of a microneedle also is very small, generally on the order of 10 nanoliters, which is difficult to reproducibly deposit using microliter and nanoliter dispensing systems in a high volume manufacturing environment. There remains a need for fast, reproducible, accurate filling of microneedle molds.

In sum, there remain needs to improve microneedle designs for better tissue insertion and to improve microneedle production methods, particularly for such improved designs.

SUMMARY

Improved microneedle arrays and drug delivery patches, along with improved methods of making microneedle arrays, have been developed which address one or more of the foregoing needs.

In one aspect, a microneedle array is provided for administration of a substance of interest into a biological tissue. In an embodiment, the array includes a base substrate having a microneedle side and an opposing back side; at least one primary funnel portion extending from the microneedle side of the base substrate; and two or more solid microneedles extending from the at least one primary funnel portion, wherein the two or more solid microneedles comprise a substance of interest. In one embodiment, each of the two or more solid microneedles further comprises a secondary funnel portion extending from the at least one primary funnel.

In another aspect, a microneedle patch is provided for administration of a substance of interest into a biological tissue. In an embodiment, the device includes a base substrate having a microneedle side and an opposing back side; a primary funnel portion extending from the microneedle side of the base substrate; and one or more solid microneedles extending from the primary funnel portion, wherein the one or more solid microneedles comprise a substance of interest and one or more matrix materials, and wherein more of the substance of interest is located in the one or more solid microneedles than is located in the primary funnel portion.

In still another aspect, a microneedle patch is provided for administration of two or more substances of interest into a biological tissue. In one case, the patch includes a base substrate having a microneedle side and an opposing back side; a first funnel portion extending from the microneedle side of the base substrate, wherein the first funnel portion is elongated in a direction parallel to the base substrate; and a first array of two or more solid microneedles extending from the first funnel portion, wherein the microneedles of the first array comprise a first substance of interest; a second funnel portion extending from the microneedle side of the base substrate, wherein the second funnel portion is elongated in a direction parallel to the base substrate; and a second array of two or more solid microneedles extending from the second funnel portion, wherein the microneedles of the second array comprise a second substance of interest, which is different from the first substance of interest.

In yet another aspect, methods are provided for making an array of microneedles. In one embodiment, the method includes (a) providing a mold having an upper surface, an opposed lower surface, and an opening in the upper surface, wherein the opening leads to a first cavity proximal to the upper surface and to a second cavity below the first cavity, wherein the first cavity defines a primary funnel portion, and wherein the second cavity defines at least one microneedle; (b) filling at least the second cavity, via the opening in the mold, with a first material which comprises a substance of interest dissolved or suspended in a first liquid vehicle; (c) drying the first material in the mold to remove at least a portion of the first liquid vehicle to form at least a tip portion of a microneedle in the second cavity, wherein the tip portion comprises the substance of interest; (d) filling the first cavity, and the second cavity if any is unoccupied following steps (b) and (c), via the opening in the mold, with a second material which comprises a matrix material dissolved or suspended in a second liquid vehicle; (e) drying the second material in the mold to remove at least a portion of the second liquid vehicle to form (i) a primary funnel portion, and (ii) any portion of the at least one microneedle unformed following steps (b) and (c), wherein the primary funnel portion comprises the matrix material; and (f) removing from the mold the at least one microneedle together with the primary funnel portion connected thereto, wherein more of the substance of interest is located in the at least one microneedle than is located in the primary funnel portion.

In another aspect, a method is provided for making an array of microneedles, which includes (a) providing a non-porous and gas-permeable mold having an upper surface, an opposed lower surface, and a plurality of openings in the upper surface, wherein each opening leads to a cavity which defines a microneedle; (b) filling the cavities, via the openings, with a fluid material which comprises a substance of interest dissolved or suspended in a liquid vehicle; (c) drying the fluid material in the mold to remove at least a portion of the liquid vehicle and form a plurality of microneedles which comprise the substance of interest; and (d) removing the plurality of microneedles from the mold, wherein the filling of step (b) is conducted with a pressure differential applied between the upper and lower surfaces of the mold.

In a further aspect, a method is provided for making an array of microneedles, which includes providing a two-part mold having a upper portion and a lower portion, the upper portion having an upper surface, an opposed lower surface, and an opening extending therethrough, the opening defining an upper cavity, the lower portion having an upper surface, an opposed lower surface, and an opening in the upper surface which is in fluid communication with the upper cavity and which leads to a lower cavity, the lower cavity defining a microneedle, wherein the upper portion and the lower portion are separably secured together; filling at least the lower cavity, via the opening in the upper portion, with a first material which comprises a substance of interest dissolved or suspended in a first liquid vehicle; drying the first material in the mold to remove at least a portion of the first liquid vehicle to form a microneedle which comprises the substance of interest; and removing the microneedle from the mold.

Additional aspects will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1:
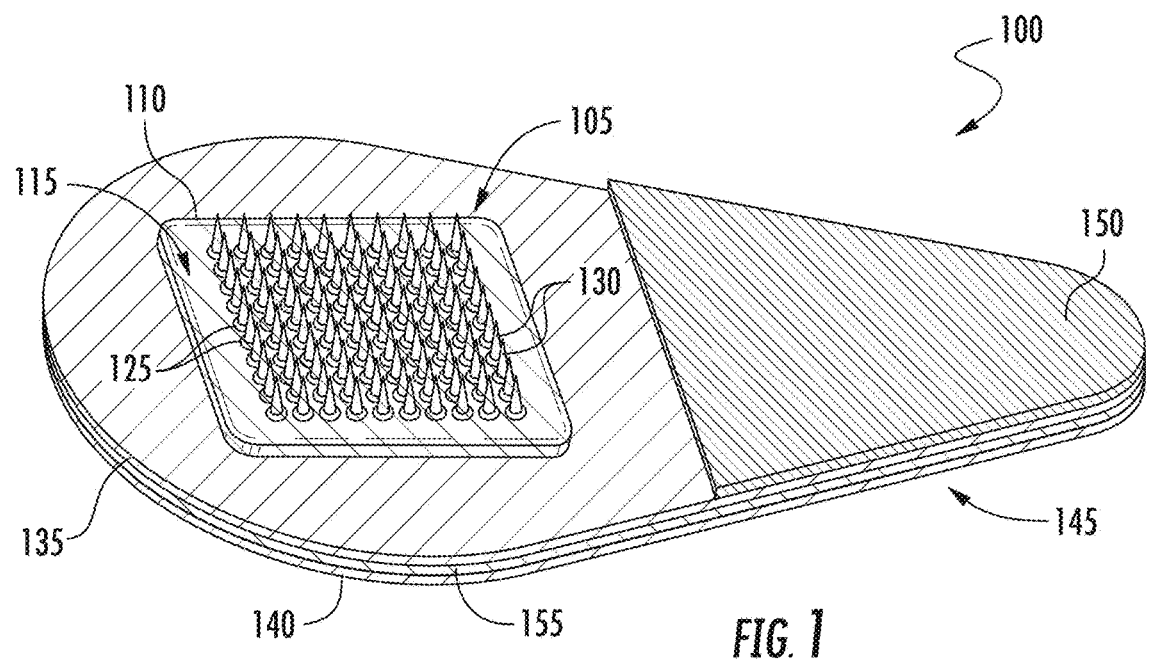
FIGS. 1-12 illustrate various embodiments of microneedle arrays, microneedle patches, and microneedle structures which include a funnel portion.

Improved microneedle arrays and methods of manufacture have been developed. In embodiments, the microneedles include an active pharmaceutical ingredient or other substance of interest, and arrays of these microneedles are particularly suited for use as/in drug delivery patches, such as for application to a patient's skin.

In embodiments, the microneedle arrays advantageously include one or more funnel portions between the base substrate and the microneedles themselves. The addition of a funnel portion (sometimes referred to herein as a "funnel," a "funnel portion," a "primary funnel portion," a "secondary funnel portion," or a "funnel lead-in") imparts certain advantages in its use, its manufacture, or in both its use and manufacturing.

First, tissue insertion difficulties may be lessened by incorporating funnels into the microneedle patch, because they raise the microneedles off their base or backing layer allowing the microneedles to more simply contact and penetrate the targeted tissue—without having to make the microneedles longer. This increases the microneedle insertion efficiency (e.g., success rate of microneedle penetration) and decreases the amount of force required to successfully apply a microneedle patch. That is, a larger number of the collection of microneedles puncture the tissue (for example, greater than or equal to 80% or 90% or 95% of the microneedles in a patch) or a larger fraction of each microneedle penetrates into the skin (for example, an average of greater than or equal to 50% or 75% or 80% or 90% of 95% of the length or the volume of the microneedles in a patch). The net result of either of these measures of microneedle penetration success rate is that a larger portion of a substance of interest being administered by the microneedles is delivered into the tissue.

This approach to microneedle design can also be forgiving, allowing microneedle insertion with little to no funnel insertion after applying a minimum force. That is, the resulting insertion depth of the microneedles with funnels is less sensitive to the application of excessive force during patch application because the rapid expansion of the funnel section hinders insertion and results in insertion up to the microneedle-funnel interface. This allows them to be inserted by simple thumb pressure alone, thumb pressure with a mechanism to indicate the minimum required force has been applied, or simpler and less aggressive applicators that may not rely on impact. For example, if an array of longer microneedles is pressed against the skin, it is possible to only partially insert the microneedles, allowing them to still penetrate shallowly. However, the actual depth of microneedle insertion is very difficult to control since the minimum force required will vary due to differences between individuals (e.g., skin types) and application sites (e.g., locations on a patient's body). Therefore, the insertion force to partially insert an array of longer microneedles will vary and by applying a force that is too small or too large will result in improper microneedle insertion depth. This is alleviated when using microneedles with funnel lead-ins because the rapid expansion of the funnel portion limits insertion depth. If the minimum force (or greater) has been applied, the insertion depth is consistent.

Second, loading and filling limits may be significantly lessened by including funnels in a microneedle device, because they increase the amount of a substance of interest that can be loaded into the microneedles during their manufacture. In a molding process that includes funnels, the amount of the substance that can be loaded is greater than the volume of the microneedle cavities multiplied by the concentration of the substance in the solution being loaded. The amount loaded can be as large as the microneedle and funnel volumes combined multiplied by the concentration of the filling solution/suspension multiplied by the number of filling steps. The funnel volume is often many times greater than the microneedle volume thereby significantly increasing the amount that can be loaded into the microneedles.

Third, manufacturing challenges can be significantly lessened by adding funnels, because they greatly increase the target area during a mold filling step, since the funnels expand out from the microneedle cavity. This larger area target (i.e., funnel-base interface) greatly relaxes the positional accuracy required for the deposition/filling system compared to a mold containing no funnels, in which the target area would be the microneedle-base interface. In addition, the volume to fill a microneedle with a funnel can be many times greater than the microneedle itself, thereby reducing this constraint too.

Other advantages and benefits of the microneedle array designs and the methods of manufacture that have been developed are described throughout the rest of the specification. Certain of the improved manufacturing methods are applicable to microneedle arrays that include funnel portions, as well as to microneedle arrays that do not include funnel portions.

Unless otherwise defined herein or below in the remainder of the specification, all technical and scientific terms used herein have meanings commonly understood by those of ordinary skill in the art to which the present disclosure belongs. It is also to be understood that the terminology used herein is for the purpose of describing particular embodiments only, and is not intended to be limiting. In describing and claiming the present embodiments, the following terminology will be used in accordance with the definitions set out below.

As used in this specification and the appended claims, the singular forms "a," "an," and "the" include plural referents unless the content clearly dictates otherwise. Thus, for example, reference to "a component" can include a combination of two or more components; reference to "a buffer" can include mixtures of buffers, and the like.

The term "about", as used herein, indicates the value of a given quantity can include quantities ranging within 10% of the stated value, or optionally within 5% of the value, or in some embodiments within 1% of the value.

1. MICRONEEDLE ARRAYS WITH FUNNEL PORTION

The microneedle arrays include a base substrate and two or more microneedles which extend from a surface of the base substrate. Each microneedle has a proximal end attached to the base substrate directly, or indirectly via one or more funnel portions, and a distal tip end which is sharp and effective to penetrate biological tissue. The microneedle has tapered sidewalls between the proximal and distal ends.

The funnel portion may be integrally formed with the microneedle. The outer surface of the funnel portion can be distinguished from the microneedle portion of the protruding structure by the distinct change/expansion in the angle of the surfaces defining the different portions of the structure, which can be seen as a rapid expansion in at least one dimension (e.g., radially) as one progresses from the distal end toward the proximal end of the microneedle. The funnel portion is wider at its base end than its microneedle end. This expansion may be designed so that little to no funnel portion is inserted into the targeted tissue layer or space.

In a preferred embodiment, a microneedle array is provided for administration of a drug or other substance of interest into a biological tissue such as skin, wherein the array includes a base substrate having a microneedle side and an opposing back side; a primary funnel portion extending from the microneedle side of the base substrate; and one or more solid microneedles extending from the primary funnel portion, wherein the one or more solid microneedles comprise a substance of interest and a matrix material, and wherein more of the substance of interest is located in the one or more solid microneedles than is located in the primary funnel portion. For example, the primary funnel portion may include from 0% to 20% of the substance of interest present in the combination of the one or more solid microneedles and the primary funnel portion from which the one or more solid microneedles extend. This embodiment advantageously avoids wasting the drug in the funnel portion.

In an embodiment, a microneedle array is provided for administration of a drug or other substance of interest into a biological tissue such as skin, wherein the array includes a base substrate having a microneedle side and an opposing back side; at least one primary funnel portion extending from the microneedle side of the base substrate; and two or more solid microneedles extending from the at least one primary funnel portion, wherein the two or more solid microneedles comprise a substance of interest. Each of the two or more solid microneedles may further include a secondary funnel portion extending from the at least one primary funnel.

Figure 2:
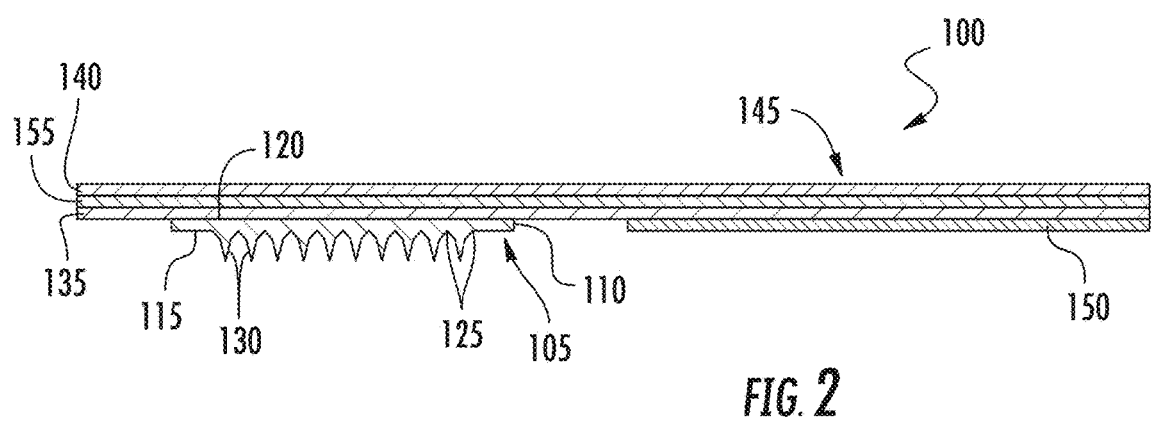

FIGS. 1-2 show one example of a microneedle array 105 as part of a microneedle patch 100, wherein each microneedle 130 extends from a funnel portion 125. The microneedle array 105 includes a base substrate 110 having a microneedle side 115 and an opposing back side 120. The funnel portions 125 extend from the microneedle side 115 of the base substrate 110. The microneedle array 105 is affixed to a handling layer 140 by an adhesive layer 135 disposed there between. The handling layer 140 includes a tab portion 145 that extends away from the microneedle array. The tab portion 145 enables a person to manually hold and manipulate the microneedle patch 100 without having to contact the microneedles 130. An adhesive cover 150 is affixed to a portion of the adhesive layer 135 that overlays the tab portion 145 of the handling layer 140. The adhesive cover 150 enables a person to manually hold and manipulate the microneedle patch 100 without having to contact the adhesive layer 135.

An optional mechanical force indicator 155 is disposed between the adhesive layer 135 and the handling layer 140. The mechanical force indicator may be used to indicate to a person the amount of force and/or pressure applied to the patch during its use. For example, in one embodiment, the indicator is configured to provide a signal when a force applied to the patch by a person (in the course of applying the patch to a patient's skin to insert the one or more microneedles into the patient's skin) meets or exceeds a predetermined threshold. The predetermined threshold is the minimum force or some amount greater than the minimum force that is required for a particular microneedle patch to be effectively applied to a patient's skin. That is, it is the force needed to cause the microneedles to be properly, e.g., fully, inserted into a patient's skin.

Structural Features of the Funnel Portion and the Microneedle

Figure 3A:
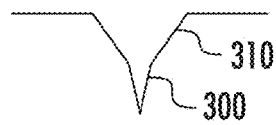
Figure 3B:
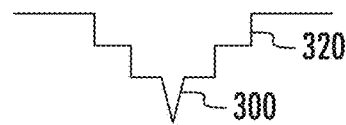
Figure 3C:
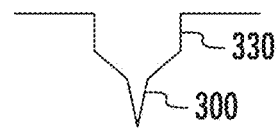
Figure 3D:
Figure 3E:
Figure 3F:

The funnel portion can be formed into a variety of different configurations. The funnel portion can have tapered walls (steeply or shallowly), 'stepped' walls, tapered walls that then become vertical, hemispherical walls, or a combination thereof. Funnel portions can be symmetric or asymmetric. Some of these configurations are illustrated in the cross-sectional views shown in FIGS. 3A-3F. FIG. 3A shows a cone shaped funnel portion 310 which has a straight tapered sidewall and microneedle 300 extending therefrom. FIG. 3B shows a funnel portion 320 with a stepped sidewall and a microneedle 300 extending therefrom. FIG. 3C shows a funnel portion 330 with a sidewall that has both a tapered portion and an untapered (vertical) portion and a microneedle 300 extending therefrom. FIG. 3D shows an axially asymmetric funnel portion 340 with a sidewall that tapers at a different angle on one side 341 of the funnel portion as compared to another (e.g., opposed) side 342 of the funnel portion, with a microneedle 301 extending therefrom. FIG. 3E shows a shallow cone shaped funnel portion 350 which has a straight tapered sidewall and a microneedle 300 extending therefrom. FIG. 3F shows a hemispherical shaped funnel portion 360 which has a curved sidewall and a microneedle 300 extending therefrom.

A single microneedle array or patch may have funnel portions having two or more different geometries. For example, an array could include one row of microneedles having funnel portions of a first size or shape and a second row of microneedles having funnel portions of a second size or shape. For example, the differences could be beneficially designed for delivering two different substances of interest.

Manufacturing and use considerations also drive the selection of the geometry of the funnel portion. For example, the density of the microneedles and funnels within an array (i.e., the spacing) may also be balanced with microneedle/funnel geometry to allow for simple needle insertion with little to no funnel insertion (i.e., because more closely space microneedles are generally more difficult to insert). As another example, during manufacturing, a volume of solution is deposited into the funnel portions of a mold and when dried/cured, the solute substantially migrates into the microneedle and its tip portion of the mold. The funnel shape, in one embodiment, is designed to promote and maximize this solute migration.

The length of a microneedle ($L_{MN}$) may be between about 50 μm and 2 mm. In most cases they are between about 200 μm and 1200 μm, and ideally between about 500 μm and 1000 μm. The length (height) of a funnel ($L_{FUN}$) may be between about 10 μm and 1 cm. In most cases funnels are between about 200 μm and 2000 μm, and more preferably between about 500 μm and 1500 μm. The ratio $L_{FUN}/L_{MN}$ may be between about 0.1 and 10, more typically between about 0.3 and 4 and more preferably between about 0.5 and 2 or between about 0.5 and 1, although a ratio between about 1 and 2 is also useful. The ratio $L_{FUN}/L_{MN}$ could be less than about 1 or could be greater than about 1. The sum $L_{MN}+L_{FUN}$ may be between about 60 um and 1.2 cm, more typically between about 300 um and 1.5 mm and more preferably between about 700 um and 1.2 mm. $L_{MN}+L_{FUN}$ can be greater than about 1 mm, or greater than about 1.2 mm or greater than about 1.5 mm.

The volume of a microneedle ($V_{MN}$) can be between about 1 nl and 100 nl. In most cases, it is between about 5 nl and 20 nl. The volume of a funnel ($V_{FUN}$) can be about 1 nl to 20,000 nl, more typically between about 5 nl and 1000 nl and more preferably between about 10 nl and 200 nl. The ratio $V_{FUN}/V_{MN}$ can be between about 0.1 to 100, more typically between about 0.5 and 20 and more preferably between about 1 and 10 or between about 2 and 5.

The cross-sectional area of the microneedle where it meets the funnel ($A_{MN-FUN}$) is between about 300 μm² and 800,000 μm². In most cases it is between about 10,000 μm² and 500,000 μm² and more preferably between about 50,000 μm² and 200,000 μm². The cross-sectional area of the funnel-base interface ($A_{FUN-BASE}$) is between about 301 μm² and 8×10⁷ μm², more typically between about 10,000 μm² and 5×10⁶ μm² and more preferably between about 100,000 μm² and 2×10⁶ μm². The ratio $A_{FUN-BASE}/A_{MN-FUN}$ is always greater than 1, because the funnel expands out from the microneedle. The ratio $A_{FUN-BASE}/A_{MN-FUN}$ is between about 1.1 to 2500, more typically between about 1.5 and 100 and more preferably between about 2 and 10.

The one or more microneedles may be arranged on a base substrate in any suitable density. For example, a plurality of microneedles may be arranged in even or staggered rows in an array, wherein each microneedle is separated from its nearest neighboring microneedle by a distance about equal to the height of the microneedle.

The width at the microneedle-funnel interface ($W_{MN-FUN}$) is between about 20 μm and 1000 μm. In most cases it is between about 100 μm and 500 μm and more preferably between about 200 μm and 400 μm. The width at the funnel-base interface ($W_{FUN-BASE}$) is between about 30 μm and 1 cm, more typically between about 300 μm and 1500 μm and more preferably between about 500 μm and 1000 μm. The ratio $W_{FUN-BASE}/W_{MN-FUN}$ is always greater than 1, because the funnel expands out from the microneedle. The ratio $W_{FUN-BASE}/W_{MN-FUN}$ can be between about 1.1 and 50, more typically between about 1.5 and 10 and more preferably between about 2 and 5.

Figure 4A:
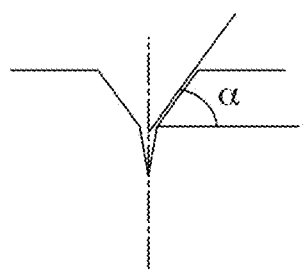
Figure 4B:
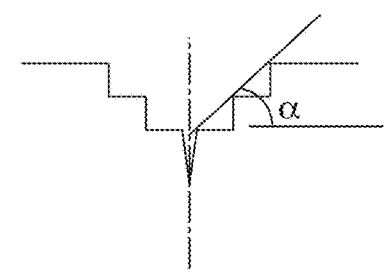
Figure 4C:
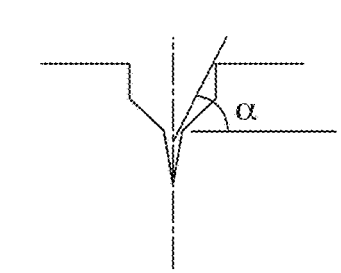

The funnel portion expands from the location where it connects to the microneedle in at least one dimension. In most cases it expands radially. The minor angle α is located between a line that extends from the funnel-microneedle interface to where the funnel portion meets the base and a line that extends from the same point and is perpendicular the central axis of the microneedle, as shown in FIGS. 4A-4C. The angle α is less than about 90°, but greater than about 10°. In most cases it is between about 30° and 75° and more preferably between about 45° and about 60°.

Each microneedle can be associated with one funnel and each funnel associated with one microneedle. Alternatively, one microneedle can be associated with more than one funnel. Alternatively, one funnel can be associated with more than one microneedle. In general, on a per patch basis the number of microneedles≥number of funnels. However, the number of funnels may exceed the number of microneedles when the funnels are used in series. The number of microneedles per patch is generally between 1 and 10,000, and in most cases is between about 20 and 1000 and more preferably between about 50 and 500. The number of funnels per patch is generally between about 1 and 10,000, and in most cases is between about 5 and 500 and more preferably between about 10 and 500. The ratio of funnels to microneedle is between about 0.01 to 10, more typically between about 0.05 and 4 and more preferably between 0.1 and 1. In some cases, the ratio of funnels to microneedle is about 1. In other cases, the ratio of funnels to microneedle is about 2 or greater. In some cases, a plurality of microneedles all in a row is associated with the same funnel. In some cases, some of the microneedles are associated with funnels and other microneedles are not associated with funnels. In some cases, the number of funnels that each microneedle is associated with within a patch is not the same for all microneedles or for all funnels.

Funnels can also be used in series, i.e., a collection of funnels where the first funnel (i.e., a primary funnel portion) (base end) feeds a number of other funnels (i.e., secondary funnel portions). For example, each microneedle may have its own funnel and a row or section of a patch of microneedles and funnels may be connected to a larger elongated funnel. This is particularly useful when filling a microneedle patch with multiple actives for one reason or another (e.g., actives are incompatible with one another, formulated differently for stability and/or release kinetics). For example, some microneedles could release the active rapidly thereby providing an immediate burst to raise the blood levels of the active into the therapeutic range quickly and other microneedles could be designed to release the active slowly to keep the blood levels of the active in the therapeutic range for an extended period of time. Alternatively, a single large funnel may be connected to an entire microneedle (with or without their own separate funnels) patch. This may be useful for filling of a single active.

FIGS. 5-8 illustrate various embodiments of microneedle arrays that comprise multiple microneedles with one funnel portion.

Figure 5:
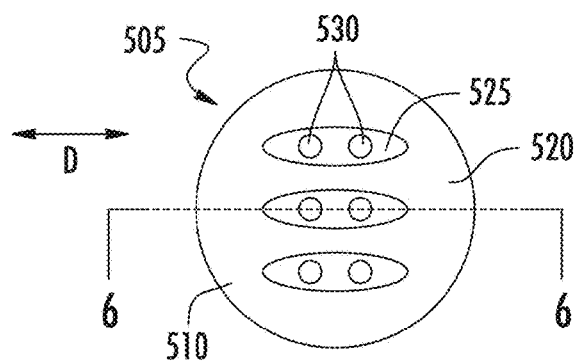
Figure 6:
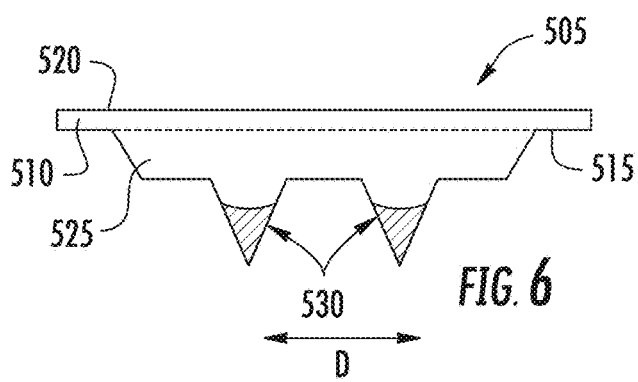

In one embodiment, as illustrated in FIGS. 5 and 6, a microneedle array 505 that includes a base substrate 510 with a microneedle side 515 and an opposing back side 520. The microneedle array 505 also includes three sets of microneedles 530 with each set having one funnel portion 525 extending from the microneedle side 515 of the base substrate 510. As shown, the microneedle tip portion includes a substance of interest, but the funnel portion 525 and base substrate portion 510 contains little to no substance of interest. Each funnel portion 525 is elongated in a direction (D) that is parallel to the base substrate 510. In this embodiment, the microneedles 530 of all three elongated funnel portions 525 contain the same substance of interest.

Figure 7:
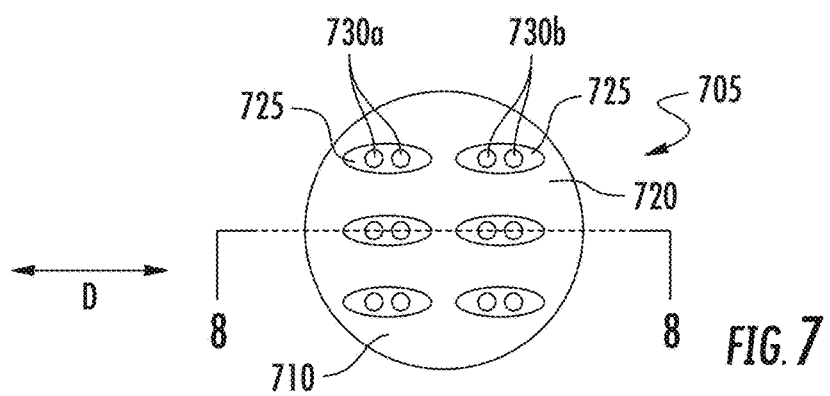
Figure 8:
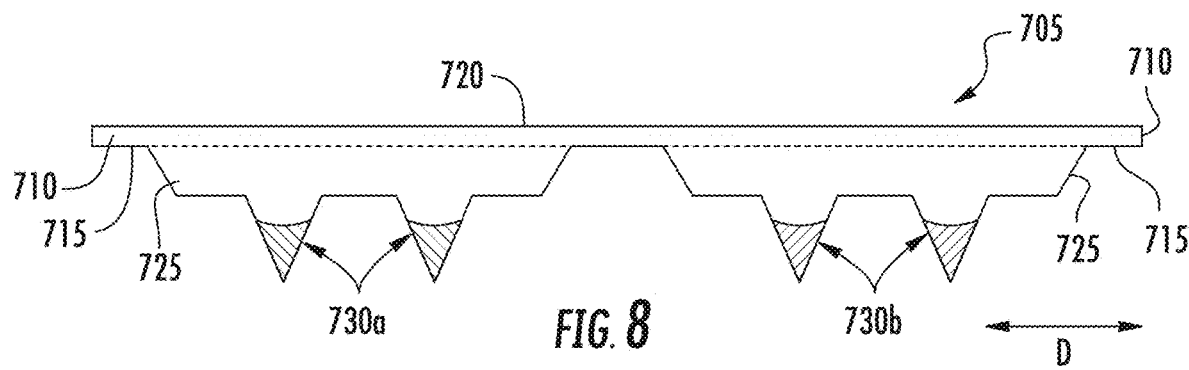

In other embodiments, different sections of the microneedle array may contain different substances of interest and/or excipients, for example, as illustrated in FIGS. 7 and 8. The microneedle array 705 includes a base substrate 710 with a microneedle side 715 and an opposing back side 720. The microneedle array 705 also includes three sets of microneedles 730a, containing a first substance of interest, and three sets of other microneedles 730b, containing a second substance of interest, with each set having one funnel portion 725 extending from the microneedle side 715 of the base substrate 710. Each funnel portion 725 is elongated in a direction (D) that is parallel to the base substrate 710.

FIGS. 9-12 illustrate various embodiments of microneedle arrays that comprise multiple microneedles with two funnel portions, a primary funnel portion and a secondary funnel portion.

Figure 9:
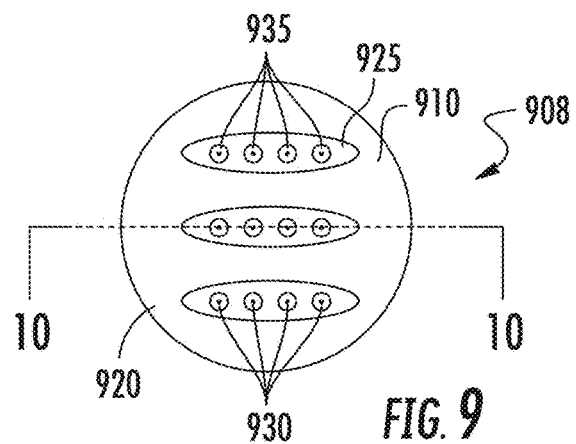
Figure 10:
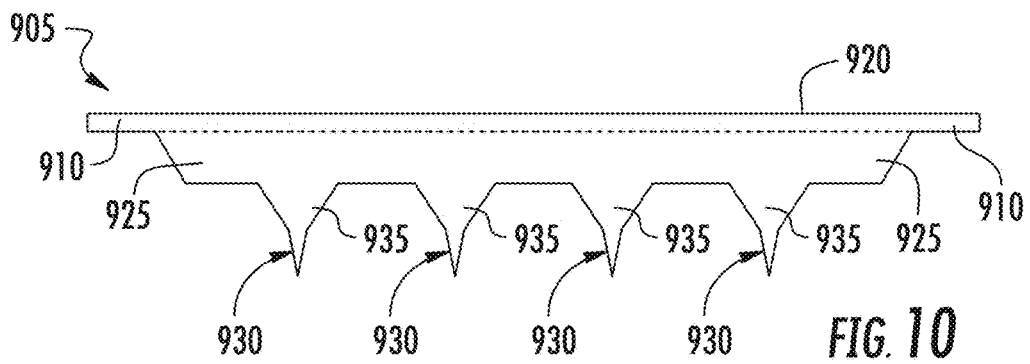

In one embodiment, as illustrated in FIGS. 9 and 10, a microneedle array 905 that includes a base substrate 910 with a microneedle side 915 and an opposing back side 920. The microneedle array 905 also includes three sets of microneedles 930 with each set having a primary funnel portion 925 extending from the microneedle side 915 of the base substrate 910 and secondary funnel portions 935 extending from the primary funnel portion 925. Each primary funnel portion 925 is elongated in a direction (D) that is parallel to the base substrate 910. In this embodiment, the microneedles 930 and funnel portions 925, 935 contain the same substances of interest and excipients, respectively.

Figure 11:
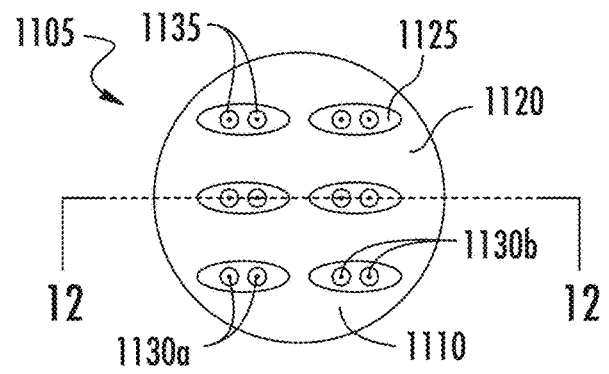
Figure 12:
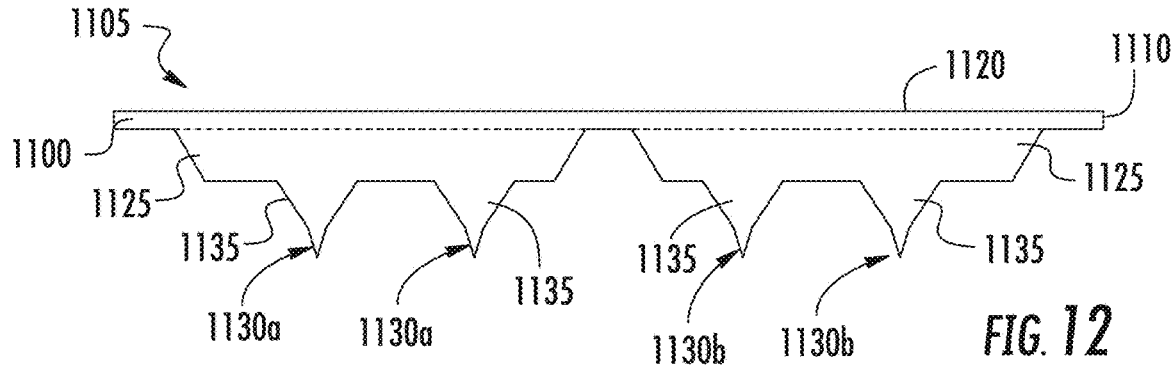

In other embodiments, different sections of the microneedle array contain different substances of interest and/or excipients, for example, as illustrated in FIGS. 11 and 12. The microneedle array 1105 includes a base substrate 1110 with a microneedle side 1115 and an opposing back side 1120. The microneedle array 1105 also includes three sets of microneedles 1130a, containing a first substance of interest, and three sets of other microneedles 1130b, containing a second substance of interest, with each set having a primary funnel portion 925 extending from the microneedle side 1115 of the base substrate 1110 and secondary funnel portions 1135 extending from the primary funnel portion 1125. Each funnel portion 1125, 1135 is elongated in a direction (D) that is parallel to the base substrate 1110.

A microneedle patch such as the foregoing could also be manufactured by automated pick-n-place type manufacturing, where each separate region of the patch containing a different formulation is molded separately and then assembled onto an adhesive pad or backing.

Figure 15:
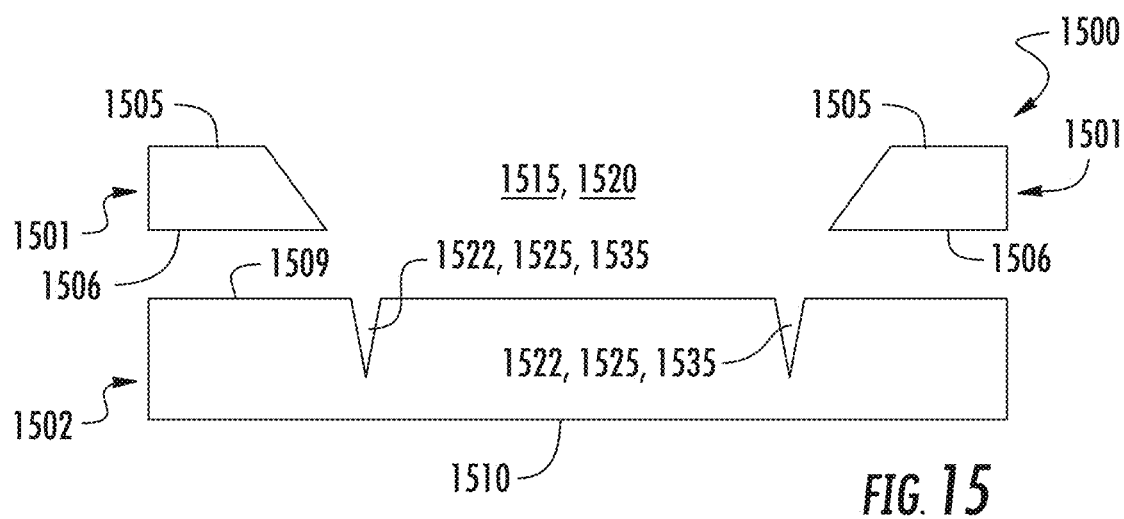
Figure 16:
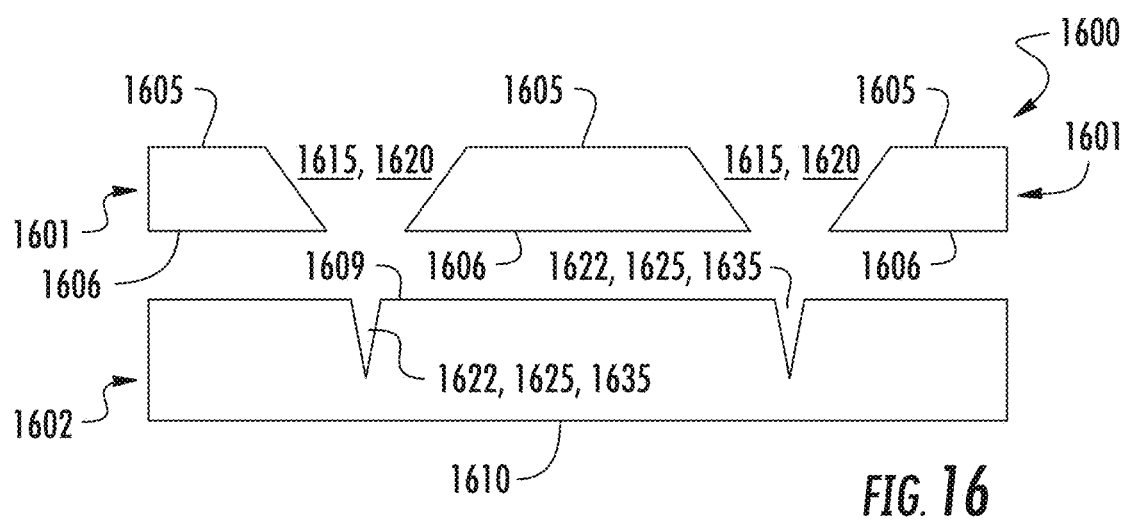

A microneedle patch may include different microneedles, for example containing different compositions of materials, including different actives and/or excipients and/or other materials. Microneedles that contain the same composition of materials may be connected to common funnel(s). In addition to different microneedles, rows, or regions having different material loaded within them, the microneedles and funnels themselves may have discrete layers of materials. The discrete layers may appear to be in a stacked, or striped, form as shown in FIG. 15, or the discrete layers may be in the form of shell layers starting from the sidewall of the cavity in the mold inward, as shown in FIG. 16.

Substance of Interest/Active Pharmaceutical Ingredient

A wide range of substances may be formulated for delivery to biological tissues with the present microneedles and methods. As used herein, the term "substance of interest" includes active pharmaceutical ingredients, allergens, vitamins, cosmetic agents, cosmeceuticals, diagnostic agents, markers (e.g., colored dyes or radiological dyes or markers), and other materials that are desirable to introduce into a biological tissue. The "substance of interest" is sometimes referred to herein as "the active." In a preferred embodiment, the biological tissue is a tissue of a human or other mammal, including but not limited to the skin of human or other mammal. In an alternative embodiment, the biological tissue is a plant tissue.

In one embodiment, the substance of interest is a prophylactic, therapeutic, or diagnostic agent useful in medical or veterinary application. In one embodiment, the substance of interest is a prophylactic or therapeutic substance, which may be referred to herein as an API. In certain embodiments, the API is selected from suitable proteins, peptides and fragments thereof, which can be naturally occurring, synthesized or recombinantly produced. Representative examples of types of API for delivery include antibiotics, antiviral agents, analgesics, anesthetics, antihistamines, anti-inflammatory agents, anti-coagulants, allergens, vitamins, antineoplastic agents.

In one embodiment, the substance of interest comprises a vaccine. Examples of vaccines include vaccines for infectious diseases, therapeutic vaccines for cancers, neurological disorders, allergies, and smoking cessation or other addictions. Some examples of current and future vaccines for the prevention of, anthrax, cervical cancer (human papillomavirus), dengue fever, diphtheria, Ebola, hepatitis A, hepatitis B, hepatitis C, Haemophilus Influenzae type b (Hib), HIV/AIDS, human papillomavirus (HPV), influenza (seasonal and pandemic), Japanese encephalitis (JE), lyme disease, malaria, measles, meningococcal, monkeypox, mumps, pertussis, pneumococcal, polio, rabies, rotavirus, rubella, shingles (herpes zoster), smallpox, tetanus, typhoid, tuberculosis (TB), varicella (chickenpox), West Nile, and yellow fever. In another embodiment, the substance of interest comprises a therapeutic agent. The therapeutic agent may be selected from small molecules and larger biotechnology produced or purified molecules (e.g., peptides, proteins, DNA, RNA). Examples of therapeutics, which may include their analogues and antagonists, include but are not limited to insulin, insulin-like growth factor, insultropin, parathyroid hormone, pramlintide acetate, growth hormone release hormone, growth hormone release factor, mecasermin, Factor VIII, Factor IX, antithrombin III, protein C, protein S, β-gluco-cerebrosidase, alglucosidase-α, laronidase, idursulphase, galsulphase, agalsidase-β, α-1 proteinase inhibitor, lactase, pancreatic enzymes, adenosine deaminase, pooled immunoglobulins, human albumin, erythropoietin, darbepoetin-α, filgrastim, pegfilgrastim, sargramostim, oprelvekin, human follicle-stimulating hormone, human chorionic gonadotropin, lutropin-α, interferon (alpha, beta, gamma), aldesleukin, alteplase, reteplase, tenecteplase, urokinase, factor VIIa, drotrecogin-α, salmon calcitonin, exenatide, octreotide, dibotermin-α, recombinant human bone morphogenic protein 7, histrelin acetate, palifermin, becaplermin, trypsin, nesiritide, botulinum toxin (types A and B), collagenase, human deoxyribonuclease I, hyaluronidase, papain, 1-asparaginase, peg-asparaginase, rasburicase, lepirudin, bivalirudin, streptokinase, anistreplase, bevacizumab, cetuximab, panitumumab, alemtuzumab, rituximab, trastuzumab, abatacept, anakinra, adalimumab, etanercept, infliximab, alefacept, efalizuman, natalizumab, eculizumab, antithymocyte globulin, basiliximab, daclizumab, muromonab-CD3, omalizumab, palivizumab, enfuvirtide, abciximab, pegvisomant, crotalidene polyvalent fab (ovine), digoxin immune serum fab (ovine), ranibizumab, denileukin diftitox, ibritumomab tiuxetan, gemtuzumab ozogamicin, tositumomab, I-tositumomab, anti-rhesus (rh) immunoglobulin G, desmopressin, vasopressin, deamino [Va14, D-Arg8] arginine vasopressin, somatostatin, somatotropin, bradykinin, bleomycin sulfate, chymopapain, glucagon, epoprostenol, cholecystokinin, oxytocin, corticotropin, prostaglandin, pentigetide, thymosin alpha-1, alpha-1 antitrypsin, fentanyl, lidocaine, epinephrine, sumatriptan, benztropine mesylate, liraglutide, fondaparinux, heparin, hydromorphone, omacetaxine mepesuccinate, pramlintide acetate, thyrotropin-alpha, glycopyrrolate, dihydroergotamine mesylate, Bortezomib, triptoreline pamaote, teduglutide, methylnaltrexone bromide, pasireotide, ondansetron hydrochloride, droperidol, triamcinolone (hex)acetonide, aripiprazole, estradiol valerate, morphine sulfate, olanzapine, methadone hydrochloride, and methotrexate.

In yet another embodiment, the substance of interest is a vitamin, herb, or dietary supplement known in the art. Non-limiting examples include 5-HTP (5-hydroxytryptophan), acai berry, acetyl-L-carnitine, activated charcoal, aloe vera, alpha-lipoic acid, apple cider vinegar, arginine, ashitaba, ashwagandha, astaxanthin, barley, bee pollen, beta-alanine, beta-carotene, beta-glucans, biotin, bitter melon, black cherry, black cohosh, black currant, black tea, branched-ahain amino acids, bromelain (bromelin), calcium, camphor, chamomile, chasteberry, chitosan, chlorella, chlorophyll, choline, chondroitin, chromium, cinnamon, citicoline, coconut water, coenzyme Q10, conjugated linoleic acid, cordyceps, cranberry, creatine, D-mannose, damiana, deer velvet, DHEA, DMSO, echinacea, EDTA, elderberry, emu Oil, evening primrose oil, fenugreek, feverfew, folic acid, forskolin, GABA (gamma-aminobutyric acid), gelatin, ginger, Ginkgo Biloba, ginseng, glycine, glucosamine, glucosamine sulfate, glutathione, gotu kola, grape seed extract, green coffee, guarana, guggul, gymnema, hawthorn, hibiscus, holy basil, horny goat weed, inulin, iron, hill oil, L-carnitine, L-citrulline, L-trypotophan, lactobacillus, magnesium, magnolia, milk thistle, MSM (methylsulfonylmethane), niacin, olive, omega-3 fatty acids, oolong tea, oregano, passionflower, pectin, phenylalanine, phosphatidylserine, potassium, probiotics, progesterone, quercetin, ribose, red yeast rice, reishi mushroom, resveratrol, rosehip, saffron, SAM-e, saw palmetto, schisandra, sea buckthorn, selenium, senna, slippery elm, St. John's wort, stinging nettle, tea tree oil, theanine, tribulus terrestris, turmeric (curcumin), tyrosine, valerian, vitamin A, vitamin B12, vitamin C, vitamin D, vitamin E, vitamin K, whey protein, witch hazel, xanthan gum, xylitol, yohimbe, and zinc.

A microneedle patch may include a single substance of interest or it may include two or more substances of interest. In the latter case, the different substances may be provided together within one of the microneedles, or some microneedles in an array of microneedles contain one substance of interest while other microneedles contain another substance of interest.

The API desirably is provided in a stable formulation or composition (i.e., one in which the biologically active material therein essentially retains its physical stability and/or chemical stability and/or biological activity upon storage). Stability can be measured at a selected temperature for a selected period. Trend analysis can be used to estimate an expected shelf life before a material has actually been in storage for that time period.

In embodiments, the substance of interest is provided as a solid that is "dry" or has been "dried" to form the one or more microneedles and becomes solubilized in vivo following insertion of the microneedle into the patient's biological tissue. As used herein, the term "dry" or "dried" refers to a composition from which a substantial portion of any water has been removed to produce a solid phase of the composition. The term does not require the complete absence of moisture (e.g., the API may have a moisture content from about 0.1% by weight and about 25% by weight).

The substance of interest may be included in a formulation with one or more excipients and other additives, as detailed below.

Matrix Material/Excipients

The matrix material forms the bulk of the microneedle, funnel portion, and backing layer. It typically includes a biocompatible polymeric material, alone or in combination with other materials. In embodiments, the matrix material, at least of the microneedles, is water soluble. In certain preferred embodiments, the matrix material includes one or a combination of polyvinyl alcohol, dextran, carboxymethylcellulose, maltodextrin, sucrose and other sugars. As used herein, the terms "matrix material" and "excipient" are used interchangeably when referring to any excipients that are not volatilized during drying and formation of the microneedles, funnels, and base substrate.

The fluid solution used in the mold filling processes described herein may include any of a variety of excipients. The excipients may consist of those that are widely used in pharmaceutical formulations or ones that are novel. In a preferred embodiment, the excipients are ones in FDA approved drug products (see the Inactive Ingredient Search for Approved Drug Products at http://www.accessdata.fda.gov/scripts/cder/iig/index.Cfm). None, one, or more than one excipient from the following categories of excipients may be used: stabilizers, buffers, bulking agents or fillers, adjuvants, surfactants, disintegrants, antioxidants, solubilizers, lyo-protectants, antimicrobials, antiadherents, colors, lubricants, viscosity enhancer, glidants, preservatives, materials for prolonging or controlling delivery (e.g., biodegradable polymers, gels, depot forming materials, and others). Also, a single excipient may perform more than one formulation role. For example, a sugar may be used as a stabilizer and a bulking agent or a buffer may be used to both buffer pH and protect the active from oxidation. Some examples of excipients include, but are not limited to lactose, sucrose, glucose, mannitol, sorbitol, trehalose, fructose, galactose, dextrose, xylitol, maltitol, raffinose, dextran, cyclodextrin, collagen, glycine, histidine, calcium carbonate, magnesium stearate, serum albumin (human and/or animal sources), gelatin, chitosan, DNA, hylaruronic acid, polyvinylpyrrolidone, polyvinyl alcohol, polylactic acid (PLA), polyglycolic acid (PGA), polylactive co-glycolic acid (PLGA), polyethylene glycol (PEG, PEG 300, PEG 400, PEG 600, PEG 3350, PEG 4000), cellulose, methylcellulose, carboxymethyl cellulose, sodium carboxymethyl cellulose, hydroxypropyl methylcellulose, acacia, Lecithin, Polysorbate 20, Polysorbate 80, Pluronic F-68, Sorbitantrioleate (span 85), EDTA, hydroxypropyl cellulose, sodium chloride, sodium phosphate, ammonium acetate, potassium phosphate, sodium citrate, sodium hydroxide, sodium carbonate, Tris base-65, Tris acetate, Tris HCl-65, citrate buffer, talc, silica, fats, methyl paraben, propyl paraben, selenium, vitamins (A, E, C, retinyl palmitate, and selenium), amino acids (methionine, cysteine, arginine), citric acid, sodium citrate, benzyl alcohol, chrlorbutanol, cresol, phenol, thimerosal, EDTA, acetone sodium bisulfate, ascorbyl palmitate, ascorbate, castor oil, cottonseed oil, alum, aluminum hydroxide, aluminum phosphate, calcium phosphate hydroxide, paraffin oil, squalene, Quil A, IL-1, IL-2, IL-12, Freund's complete adjuvant, Freund's incomplete adjuvant, killed *Bordetella pertussis, Mycoobacterium bovis*, and toxoids. The one or more selected excipients may be selected to improve the stability of the substance of interest during drying and storage of the microneedle devices, as well providing bulk and/or mechanical properties to the microneedle array.

2. MICRONEEDLE PATCH

The microneedle array described above may be combined with one or more other components to produce a microneedle patch, such as a patch that can be manually applied to the skin of a patient. For example, the microneedle array may be combined with an adhesive layer, which may be used to facilitate securing the patch to a patient's skin during the period of administration of the substance of interest. A backing or handle layer may further be included to facilitate handling of the patch, as described above and illustrated in FIGS. 1 and 2.

The backing layer may be made out of a variety of materials, and may be the same or different than the tab portion. In some embodiments, the backing layer may be a composite material or multilayer material including materials with various properties to provide the desired properties and functions. For example, the backing material may be flexible, semi-rigid, or rigid, depending on the particular application. As another example, the backing layer may be substantially impermeable, protecting the one or more microneedles (or other components) from moisture, gases, and contaminants. Alternatively, the backing layer may have other degrees of permeability and/or porosity based on the desired level of protection. Non-limiting examples of materials that may be used for the backing layer include various polymers, elastomers, foams, paper-based materials, foil-based materials, metallized films, and non-woven and woven materials.

A microneedle patch may be stored in protective packaging prior to use. In one case, the microneedle patches are combined with a storage tray. One or more trays may be disposed in a flexible container (e.g., pouch) and/or rigid container (e.g., box). In some embodiments, a lid may be disposed on the tray to protect the microneedle patch prior to use. Such lids may be the same or a different material from the tray, and may be sealed to the perimeter of the tray (i.e., using a heat seal, cold seal, or pressure sensitive adhesive). In one embodiment, a desiccant may be provided in the recessed regions or in the flexible or rigid container housing the tray. A desiccant may alternatively or in addition be part of the tray itself. For example, a desiccant material may be included (e.g., dispersed in or coated onto) the material forming the structure of the tray. For example, the tray may be formed of a desiccant polymer known in the art. The desiccant may be used to complete the drying of the microneedles after removal from the production mold.

In one embodiment, the microneedle patch includes an array of several microneedles, e.g., from 10 to 1000 microneedles. In a preferred embodiment, the microneedles are solid microneedles that include a substance of interest, such as an active pharmaceutical ingredient (API), which becomes solubilized in vivo following insertion of the microneedle into a biological tissue, e.g., into the skin of a patient. For example, the substance of interest may be mixed into a water soluble matrix material forming a solid microneedle extending from a base substrate. The substance of interest is provided in a formulation referred to herein as being "dissolvable." In embodiments in which the substance of interest and a matrix material in which the substance of interest is dispersed form the structure of the microneedle, the matrix material also preferably is dissolvable in vivo, such that the entire microneedle dissolves in vivo.

In one embodiment, the microneedles within a given patch all contain the same active and excipients. However, the actives and/or the excipients may be different in each microneedle, in different rows of microneedles, or sections/regions of the microneedle array. Possible reasons for designing the microneedle patch with such segregation are: i) the different actives are incompatible with one another, ii) the different actives require different stabilizing excipients, and iii) different release profiles (e.g., combination of rapid bolus followed by a sustained release) are desired of a single active or of different actives. Examples are different arrays and patches are described in FIGS. 5-12.

3. METHOD OF MAKING MICRONEEDLE ARRAYS

Embodiments of the manufacturing methods described herein are used to make microneedle arrays, which, generally described, include a base substrate with one or more microneedles extending from the base substrate. Generally speaking, the method includes a molding process, which advantageously is highly scalable. The process entails providing a suitable mold; filling the mold with suitable fluidized materials; drying the fluidized material to form the microneedles, the funnel portions if included, and the base substrate; and then removing the formed part from the mold. These filling and drying steps may be referred to herein as "casting."

Figure 13:
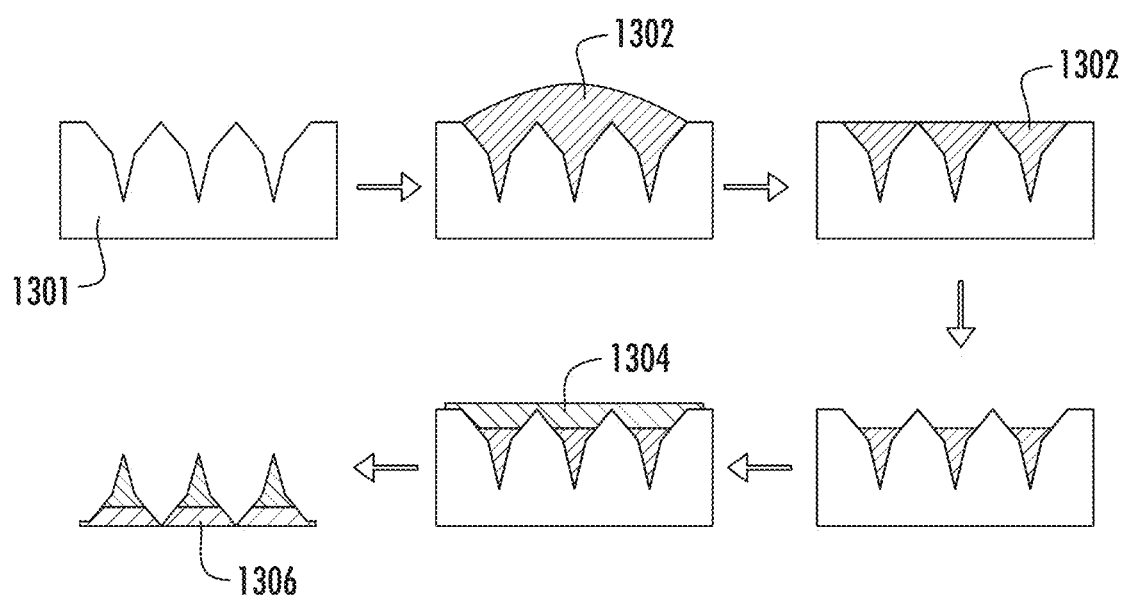
FIGS. 13-16, 18-21, and 25-27 illustrate various methods, molds, and systems for making microneedle arrays, as described herein.
Figure 25:
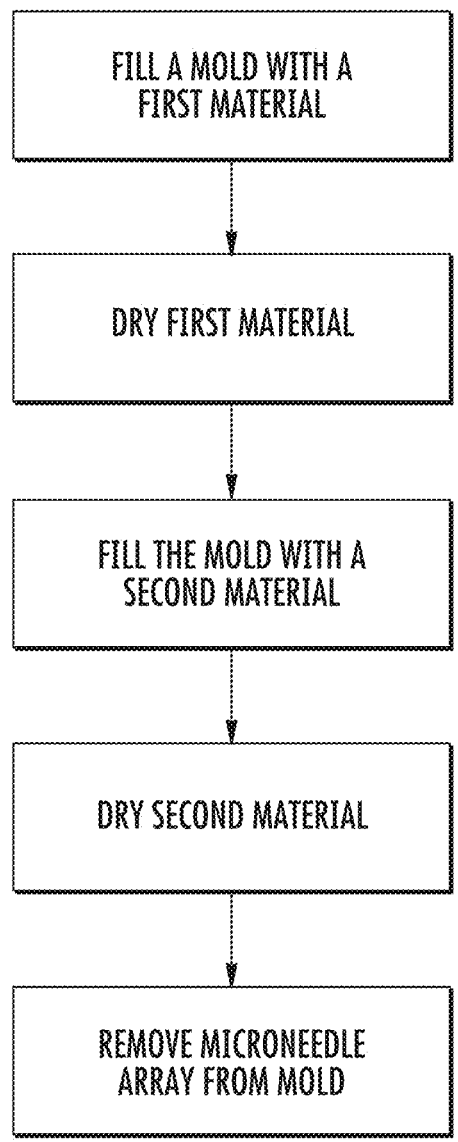

FIG. 13 illustrates one embodiment of a molding process that includes two castings. In this embodiment, a mold 1301 is provided and then filled with a first fluidized material 1302, followed by drying the first fluidized material 1302 thereby forming microneedles of a microneedle array 1306. After which, the mold 1301 is filled with a second fluidized material 1304, followed by drying the second fluidized material 1304 thereby forming a corresponding funnel portion for each microneedle of the microneedle array 1306. The microneedle array 1306 is then removed from the mold 1301. In a preferred embodiment, the first fluidized material 1302 includes a drug or other substance of interest, and the second fluidized material 1304 does not include a drug or other substance of interest. A process flow diagram of one method of making the microneedle arrays as described herein is illustrated the block flow diagram shown in FIG. 25.

In a preferred embodiment, a method is provided for making an array of microneedles, which includes (a) providing a mold having an upper surface, an opposed lower surface, and an opening in the upper surface, wherein the opening leads to a first cavity proximal to the upper surface and to a second cavity below the first cavity, wherein the first cavity defines a primary funnel portion, and wherein the second cavity defines at least one microneedle; (b) filling at least the second cavity, via the opening in the mold, with a first material which comprises a substance of interest dissolved or suspended in a first liquid vehicle; (c) drying the first material in the mold to remove at least a portion of the first liquid vehicle to form at least a tip portion of a microneedle in the second cavity, wherein the tip portion comprises the substance of interest; (d) filling the first cavity, and the second cavity if any is unoccupied following steps (b) and (c), via the opening in the mold, with a second material which comprises a matrix material dissolved or suspended in a second liquid vehicle; (e) drying the second material in the mold to remove at least a portion of the second liquid vehicle to form (i) a primary funnel portion, and (ii) any portion of the at least one microneedle unformed following steps (b) and (c), wherein the primary funnel portion comprises the matrix material; and (f) removing from the mold the at least one microneedle together with the primary funnel portion connected thereto, wherein more of the substance of interest is located in the at least one microneedle than is located in the primary funnel portion. The matrix material in step (e) may further form a base substrate connected to the primary funnel portion distal to the at least one microneedle. In a preferred embodiment, the percentage of the substance of interest located in the at least one microneedle is at least 50%, more preferably 60%, more preferably 70%, more preferably 80% and more preferably 90%. Typically, this percentage represents the average percentage among the microneedles loaded with the substance of interest within a microneedle patch.

In another preferred embodiment, a method is provided for making an array of microneedles, which includes (a) providing a non-porous and gas-permeable mold having an upper surface, an opposed lower surface, and a plurality of openings in the upper surface, wherein each opening leads to a cavity which defines a microneedle; (b) filling the cavities, via the openings, with a fluid material which comprises a substance of interest dissolved or suspended in a liquid vehicle; (c) drying the fluid material in the mold to remove at least a portion of the liquid vehicle and form a plurality of microneedles which comprise the substance of interest; and (d) removing the plurality of microneedles from the mold, wherein the filling of step (b) is conducted with a pressure differential applied between the upper and lower surfaces of the mold. This advantageously can enable filling, particularly of viscous materials, at useful rates. For example, the pressure differential can be achieved by applying a pressure greater than atmospheric to the upper surface, applying a pressure smaller than atmospheric to the lower surface or a combination of both.

In another embodiment, a method is provided for making an array of microneedles, which includes providing a two-part mold having a upper portion and a lower portion, the upper portion having an upper surface, an opposed lower surface, and an opening extending therethrough, the opening defining an upper cavity, the lower portion having an upper surface, an opposed lower surface, and an opening in the upper surface which is in fluid communication with the upper cavity and which leads to a lower cavity, the lower cavity defining a microneedle, wherein the upper portion and the lower portion are separably secured together; filling at least the lower cavity, via the opening in the upper portion, with a first material which comprises a substance of interest dissolved or suspended in a first liquid vehicle; drying the first material in the mold to remove at least a portion of the first liquid vehicle to form a microneedle which comprises the substance of interest; and removing the microneedle from the mold.

Methods for manufacturing microneedle arrays and patches preferably are performed under a minimum ISO 5 (100) process, an ISO 7 process, or an ISO 8 process. Terminal sterilization may be utilized when compatibility of the sterilization method with the active has been demonstrated.

The Mold

In embodiments, the mold used to manufacture microneedle arrays contains cavities that are the negative of the microneedles, and of any funnel portions, to be produced. In some embodiments, the mold includes a funnel section that is only used to increase the loading within the microneedle and then is removed before processing the full microneedle array. In those embodiments, the mold may be a two-part mold or include a separate filling template. Some of the novel methods of making microneedles described herein may be used to make microneedles that extend from a base substrate and do not include a funnel portion.

The molds can be formed from a single part or multiple parts. In one embodiment, the two-part mold consists of a upper mold portion having one or more cavities defining a funnel portion and a lower mold portion having one or more cavities defining one or more microneedles. The mold portions may be permanently or reversibly secured to one another. Molds consisting of two or more parts can be aligned and reversibly or irreversibly connected to one another by applying pressure (e.g., pneumatic, mechanical force or clamp), adhesive, magnetic/electrical charge, surface tension, chemical bonding (i.e., covalent, non-covalent), or vacuum.

Figure 14:
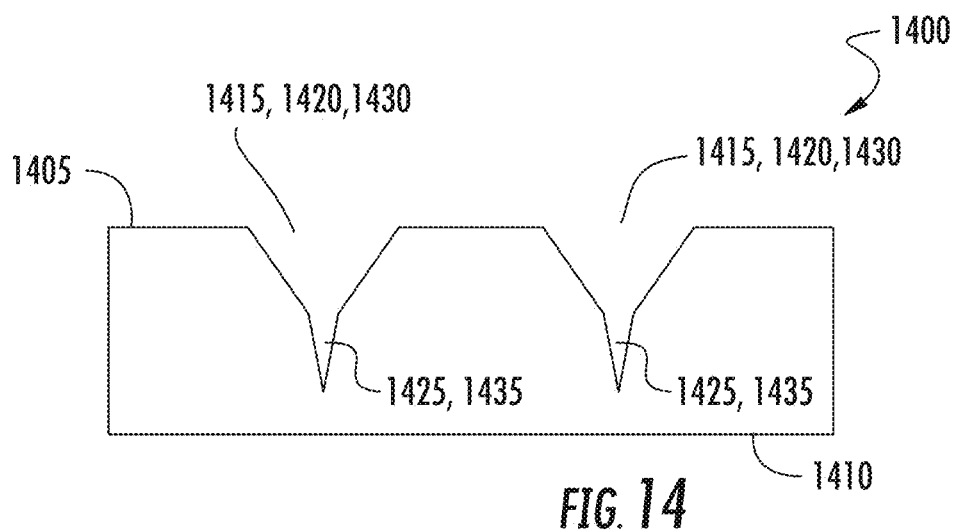

Examples of various molds are illustrated in the cross-sectional views of FIGS. 14-16. FIG. 14 shows an embodiment of a single part mold 1400 having an upper surface 1405 and a lower surface 1410. The upper surface 1405 has openings 1415, wherein each opening 1415 leads to a first cavity 1420 proximal to the upper surface 1405 and a second cavity 1425 that extends from the first cavity 1420 in a direction away from the upper surface 1405. The first cavity 1420 defines a primary funnel portion 1430 and the second cavity 1425 defines a microneedle 1435. FIGS. 15 and 16 show embodiments of two-part molds. FIG. 15 shows one embodiment of a two-part mold 1500 having an upper portion 1501 separably secured to a lower portion 1502. The upper portion 1501 includes an upper surface 1505, an opposed lower surface 1506, and an opening 1515 extending therethrough, wherein the opening 1515 defines an upper cavity 1520. The lower portion 1502 includes an upper surface 1509, an opposed surface 1510, and openings 1522 in the upper surface 1509. The openings 1522 are in fluid communication with the upper cavity 1520, and each opening 1522 leads to a lower cavity 1525 that defines a microneedle 1535.

FIG. 16 illustrates another embodiment of a two-part mold 1600 having an upper portion 1601 separably secured to a lower portion 1602. The upper portion 1601 includes an upper surface 1605, an opposed lower surface 1606, and openings 1615 extending therethrough, wherein each opening 1615 defines an upper cavity 1620. The lower portion 1602 includes an upper surface 1609, an opposed surface 1610, and openings 1622 in the upper surface 1609. Each opening 1622 is in fluid communication with a corresponding upper cavity 1620, and leads to a lower cavity 1625 that defines a microneedle 1635.

In one embodiment, the upper cavity serves as a filling cap during the filling of the lower cavity. That is, the upper cavity is configured not a funnel but instead as a structure useful to keep the liquid material in place over/above the opening during the drying process, at least until the material is sufficiently solidified that it will not flow away. The filling cap may be discarded after formation of the microneedles.

The molds may be reusable or disposable. With traditional molding processes, the molds are costly and are generally composed of hardened steel, which can be used over and over to create, for example, millions of parts. Since the mold/tooling cost is spread out over many parts, that process is still economical. However, low-cost single-use molds are also of interest. For example, molds made of elastomers manufactured by casting or direct machining techniques (e.g., laser ablation) can be inexpensive to make. Also, their elastomeric properties allow the microneedle arrays to be more gently removed from the molds versus rigid mold materials. Often disposable manufacturing tools are preferred in pharmaceutical and/or aseptic manufacturing because they have advantages from a sterility and cleanliness perspective (e.g., no rigorous cleaning methods or cleaning validations to ensure the active has been fully removed between manufacturing batches).

The geometries of the molds are generally the inverse of the microneedle arrays to be produced. The molds essentially have the same geometries (in inverse form) as the geometries described above for the microneedles and funnels.

In general, the molds can be open (i.e., no top portions) for casting or similar type filling processing, or they can have separate top portions that are compatible with a pressure driven or injection molding type filling process. The molds can be sized to produce an individual microneedle (i.e., single cavity), more than one microneedle array (i.e., multi-cavity) in the form of a sheet or plate, or multiple arrays of microneedles, which in turn can be assembled into patches. In one case, the molds can be the form of a flexible roll that is fed through a continuous reel-to-reel process, an embodiment of which is shown in FIG. 19.

Figure 19:
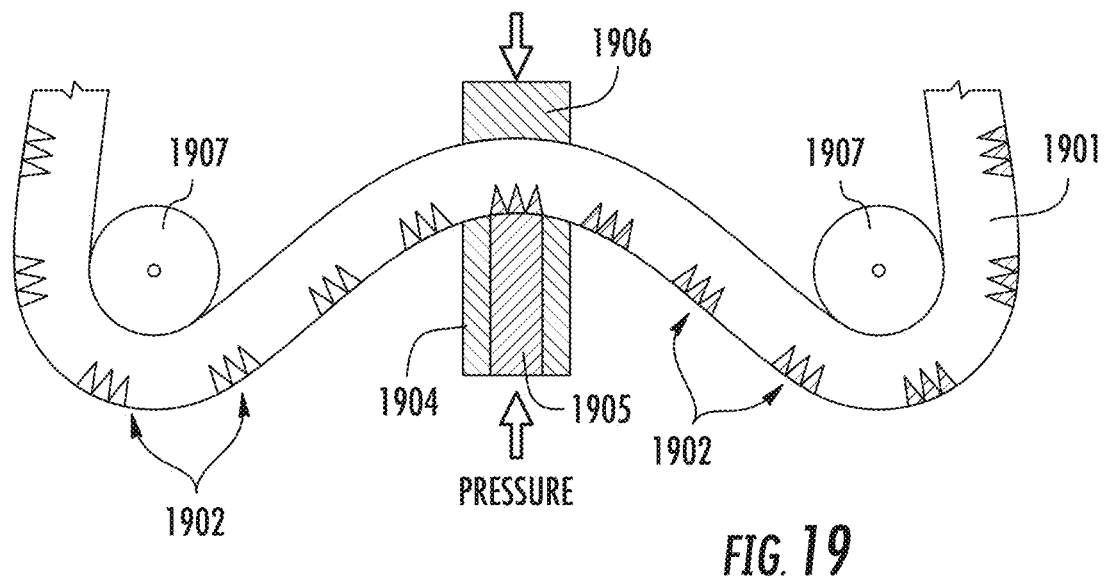
Figure 20:
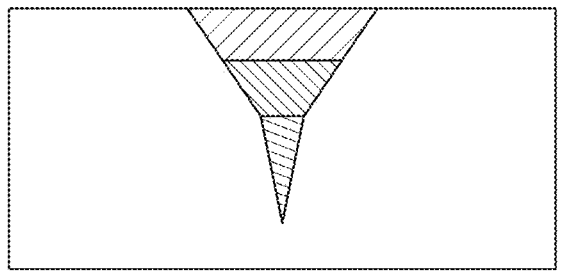
Figure 21:
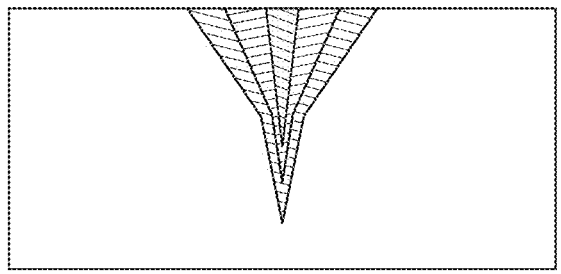

FIG. 19 is a cross-section view of one example of a system for use in a continuous filling process. It shows part of a loop of flexible mold 1901 which include spaced microneedle cavity arrays 1902. The mold 1901 is fed by rollers, or reels, 1907 through a stationary filling station that includes pressure/fill head 1904. The pressure/fill head 1904 includes a reservoir 1904 containing a fluid 1905 that, under pressure, is driven into the cavities of the arrays 1902. Stationary plate 1906 contacts the back ("lower") side of the mold 1901 and secures/stabilizes the mold about the cavity array 1902 being filled, providing an opposing force against the mold to provide a fluid tight interface between the pressure/fill head 1904 and the mold 1901. In embodiments, the stationary plate 1906 may be a vacuum plate, providing a pull force on the bottom of the mold to complement the push force on the top of the mold. The filled microneedle arrays are then moved to other positions, downstream, for further processing.

The mold may be manufactured from a variety of materials including, but not limited to metals, polymers, ceramics, elastomers, composites, etc. or a combination of these or other materials. The molds may be solid, may contain discrete pores/voids, and/or may be permeable to gases but have very low or no permeability to liquids, such as the processing solvents (liquid vehicles) of interest. Examples of suitable processing solvents include water and organics solvents, such as volatile organic solvents known in the art of polymer molding.

In one embodiment, the mold is made of silicone (e.g., polydimethylsiloxane, PDMS), which is permeable to air, but not very permeable to water and other solvents. This enables the air to be removed from microneedle/funnel cavities of the mold through the mold walls via a pressure gradient from inside the mold cavities (high) to outside the mold (low). This process advantageously is more scalable and suited for an aseptic environment versus, for example, applying vacuum around the entire system as described in the literature. The PDMS advantageously does not contain discrete interconnected pores like porous metal or porous ceramic molds. These discrete pores may become clogged with dried excipients causing them to be taken offline and replaced and/or aggressively cleaned. The PDMS mold is also elastomeric, which beneficially provides for a very gentle demolding process that does not require release agents/coatings, unlike rigid mold materials. Microneedle tips may break off in a mold during the demolding process when using rigid molds. This would produce inferior microneedles and would require the molds to be aggressively cleaned before reuse. With a suitable elastomeric (e.g., PDMS) mold, the chance of microneedle breaking is lower, and the molds can be manufactured inexpensively enabling them to be single-use molds, if desired.

In particular embodiments, the molds have much greater permeability to air than to water or other liquid solvents (such that they are configured/effective to enable the removal of air from molds during microneedle manufacturing by a pressure gradient across the mold walls) and lack an interconnected porous structure. In particular embodiments, the molds are made of materials that are flexible/elastomeric (such that they are configured/effective to mold and demold without the use of release agents/coatings, to effect demolding by deforming the mold, and/or to enable cost effective single use molds).

The molds preferably are made of materials that produce no or minimal leaching or dusting. The materials of construction of the molds are selected to be compatible with the substance of interest, excipients, disinfectants (e.g., ethanol, isopropanol), one or more common sterilization methods (e.g., heat, steam, ethylene oxide, irradiation, chemical, UV light), and other processing materials used to form the microneedle arrays.

In optional embodiments, the molds are coated with a material that serves as a release agent so that the microneedle arrays/patches are more easily removed from the mold. The molds may have ejection pins or similar mechanical structures to aid in microneedle array/patch removal.

In a preferred embodiment, the mold surfaces, e.g., the surfaces of the cavities in contact with and defining the microneedles and funnels, should be smooth. Minimal surface roughness aids with a cleaner filling process (i.e., more active transferred to the microneedle and its tip versus the sidewalls of the funnels), demolding the microneedle patch from the mold, and reduces friction during microneedle insertion (i.e., smooth-walled molds create smooth-walled microneedles that have less frictional losses during insertion than microneedles with rough surfaces). The surface roughness average (Ra) should be less than 10 microns, preferably less than 1 micron, and more preferably less than 0.1 microns.

The molds may be made by grinding, milling (e.g., conventional milling, micromilling, nanomilling), drilling, laser processing (e.g., ablation, drilling), electrodischarge machining (e.g., EDM, microEDM), wet and/or dry etching, 3D printing, electroforming, lithography (e.g., UV, stereolithography), etc. In a preferred embodiment, the mold is formed by making a casting of a master structure. The master structure can be machined using the techniques described herein or otherwise known in the art for mold manufacturing. The geometry of the master structure can be the same geometries as the geometries described herein for the microneedles.

Although the foregoing molds and molding casting processes may be described with reference to manufacturing a single microneedle patch, the molds may be configured to form a plurality of microneedle patches. For example, in embodiments the mold may be configured to produce 6 or more patches, 12 or more patches, and the like.

Filling

The composition of the filling solutions generally reflects the desired materials in the final microneedle array, with the exception of the solvents that may be substantially removed during the process.

In a preferred embodiment, the substance of interest is loaded preferentially into the microneedles and their tips, and not into the funnel portions. The substance of interest is part of a filling material that is transferred into the mold. The filling material may also include a liquid vehicle. The filling material may be in the form of a solution, slurry or suspension of particles, melt, powder or particles, or a combination of any of these forms. One or more of these forms may be used in a multi-step filling process. This "filling material" may be referred to herein as a "solution" or as a "fluid material".

In various filling steps, the filling material may include a liquid vehicle. The term "liquid vehicle" may be referred to herein as a "solvent" or a "carrier fluid." In various embodiments, the filling material may include (1) only the solvent, (2) no solvent, (3) only a matrix material, (4) a combination of a solvent and a matrix material with no substance of interest, (5) a combination of only a solvent and a substance of interest, or (6) a combination of a solvent, a substance of interest, and a matrix material. The solvent may be water, an organic solvent, such as a volatile organic solvent, or a combination thereof. Some examples are Class 3 solvents that include acetic acid, heptane, acetone, isobutyl acetate, anisole, isopropyl acetate, 1-butanol, methyl acetate, 2-butanol, 3-methyl-1-butanol, butyl acetate, methylethyl ketone, tert-butylmethyl ether, methylisobutyl ketone, dimethyl sulfoxide, 2-methyl-1-propanol, ethanol, pentane, ethyl acetate, 1-pentanol, ethyl ether, 1-propanol, ethyl formate, 2-propanol, formic acid, and propyl acetate.

The microneedle and funnel cavities may be completely filled, partially filled, or overfilled. After a filling step occurs, it is generally followed by a drying or curing step. The curing step can be achieved by heating or reduction in pressure (e.g., to evaporate solvent), by cooling or elevation of pressure (to solidify matrix material), exposure to light (e.g., polymerization due to ultraviolet light exposure) or combinations of these. This drying or curing step may fully, substantially or only partially dry or cure the deposited material. In general, the solution transfers more of the active into the microneedle and their tips when its viscosity is low, it has high surface energy within the funnel, and is not saturated with active (i.e., active is highly soluble in the solvent). However, none of these three characteristics are required, they just typically enable more preferential loading of the microneedles and their tips.

In a preferred embodiment, a two-step filling process is used, wherein the first filling step contains the substance of interest, which substantially migrates into the microneedle and its tip during the drying/curing process. This is followed by a second filling step and a subsequent drying/curing process. This second filling step contains the matrix material(s) that give the microneedles and funnels their mechanical structure and may be overfilled to create the base substrate or part of the base substrate.

In other embodiments, a single filling step or more than two filling steps may be used. A single filling step may be desirable, for example, if the active is inexpensive and the excess active in the funnel and base can be wasted. More than two filling steps may be desirable to further increase the loading of the active in the microneedles above and beyond the funnels' enhancement, further target the active within the microneedles and their tips, deposit multiple actives or excipients in discrete layers within the microneedles, deposit multiple actives or excipients within different needles or sections of needles within a given microneedle patch and/or impart further functionality into the microneedle patch (e.g., insert a rapidly dissolving or fracturable layer where the microneedles meet their funnels to allow for rapid separation of the microneedles thereby significantly decreasing required administration time).

One embodiment of a process that includes more than two-filling steps is as follows: The molds may be filled with a first solution containing an active (as well as possible excipients), which is then dried. The mold is filled again with the same solution and dried. This can be repeated until the desired quantity of active is loaded into the microneedles. This is followed by one or more final filling steps in which the molds are filled with excipients (which could be the same and or different excipients as in prior fillings) and without active, which provide the microneedles with their mechanical structure once dried.

Another embodiment of a process that includes more than two-filling steps is as follows: Although the funnels allow for preferential filling of the microneedles with active (as well as possible excipients), some of the active may deposit on the sidewalls of the funnels. This is more pronounced as the solutions become more viscous and/or supersaturated during the drying process. Therefore, one or more 'rinsing' steps may be inserted into the process that will carry the active further down into the microneedles (i.e., towards the microneedle tips). The rinsing steps will consist of a solvent or carrier for the active (as well as possible excipients) but containing no active. As the solvent or carrier fills the funnels, it redissolves or 'picks up' active and transports it into the microneedle as it migrates into the microneedle cavity. This is followed by final filling step(s) in which the molds are filled with the excipients (which could be the same and or different excipients as in prior fillings) and without active, which provide the microneedles with their mechanical structure once dried.

In one embodiment, the filling process includes a first filling which uses a volume of solution that is substantially equal to or less than the volume of the microneedle plus the funnel cavity and preferably greater than the volume of the microneedle cavity. This filling process is most amenable to filling with droplets of the specified volume. The microneedle+funnel volume is the sum of the volume(s) of the microneedle cavity(ies) that are all being filled at that time during the filling process and the volume(s) of the funnel(s) that are connected to these microneedle cavity(ies) being filled. In one embodiment, the filling process includes a second filling which uses a volume of solution that is substantially equal to or greater than the volume of the microneedle+funnel cavity. The filling process may combine these first and second filling steps as described above in this paragraph.

In embodiments, the filling step includes one or more features or sub-steps that enhance preferential loading of the fluid or the substance of interest into the microneedles versus the funnel portions. Combinations of the following embodiments are envisioned.

In one embodiment, the funnel portion is provided with a relatively steep funnel angle. By having a steeper funnel angle, it allows for gravity (or an applied pressure gradient) to further influence flow of the solution down (i.e., towards the microneedle tips) the sidewalls of the mold as it is drying. For this reason, microneedle and mold geometries may include steep funnel angles. Here and elsewhere in this disclosure reference to movement "down" does not necessarily refer to an orientation relative to gravity, but refers to an orientation relative to the mold, such that "down" refers to movement toward the microneedle tip.

In one embodiment, at least the funnel portion of the mold cavity is provided with smooth sidewalls. By having smooth sidewalls, it helps the solution migrate into the microneedles as it dries. The solution is less likely to become caught in cracks and crevices, and it will have less frictional resistance to flow driven by gravity, surface tension, pressure-driven convection, vibration, electrophoresis/electroosmosis and other forces.

In one embodiment, the microneedle portion of the mold is provided with a lower surface tension than in the funnel portion. By having a relatively higher surface tension in the funnel portion and a relatively lower surface tension in the microneedle portion of the mold, the solution will more easily and cleanly migrate down the funnel and into the microneedle portion of the mold. Surface tension can be influenced by both the solution properties and the mold surface. Accordingly, the surface tension may be altered by selection and use of surfactants, oils, mold surface roughness, coatings, etc.

In one embodiment, the filling solution is provided to have a low viscosity. A fill solution having a relatively low viscosity is more fluid and as it dries it can more easily flow down into the microneedles. In embodiments in which the solution includes the active, it is generally preferred that the viscosity of the solution be less than about 100 cp, more preferably less than about 50 cP, more preferably less than about 10 cP, or more preferably less than about 5 cP.

In a particularly useful and preferred embodiment, the filling process includes a rinse step. This "rinse down" or "rinse" step may be used to further preferentially load the microneedles and their tips. In a rinse step, after filling with the active and drying/curing, the molds may be refilled with a solvent/carrier to redissolve or pick up the active and carry it down into the microneedle cavities where it can resettle. The rinse down step rinses active off the walls of the funnel and transfers it into the microneedle. Therefore, in one embodiment, the molding process includes at least three casting processes in the following order: a casting process that deposits active in the mold, a casting process that "rinses" active further down into the mold (i.e., with the objective of removing active from the funnel portion of the mold and moving it into the microneedle portion and/or tip of the microneedle portion of the mold), a casting process that deposits excipient(s) which provide the microneedles with their mechanical structure once dried.

In one embodiment, vibration or ultrasound is applied to the mold to facilitate movement of the active move downward from the funnel and toward the microneedle during drying. The vibration will help more of the solution/active find the point of lowest energy in the mold (i.e., microneedles and their tips).

In one embodiment, the filling step includes application of an electromagnetic field, or a combination thereof, to the filling material. For example, electrophoresis, electroosmosis, magnetophoresis, or other mechanisms mediated by electric and magnetic fields may be used.

In one embodiment, a pressure is applied to the fluid to further aid migration of the solution towards and into the microneedle cavities. The pressure can be applied in the form of flowing sterile air/nitrogen (i.e., a blower) or similar methods for creating a pressure gradient to help drive the solution down as it dries.

In one embodiment, a vacuum is applied to the bottom side of the mold, wherein the mold includes discrete pores or wherein the mold is permeable to air. Such a vacuum can help pull the solution down into the microneedle cavities as it dries.

In one embodiment, a positive pressure is applied to the top side of the mold, wherein the mold includes discrete pores or wherein the mold is permeable to air. Such a positive pressure can help push the solution down into the microneedle cavities as it dries.

In one embodiment, a centrifuge or similar device is used to spin the molds to create a force normal and into the molds, creating a gravitational force to drive the solution down into the microneedles as it dries/cures. This process also can useful be to drive larger molecules (e.g., the active) down into the microneedles and their tips while the filling fluid is still in the solution state. The term "larger molecules" is used to mean molecules that are larger than those of the liquid vehicle, or solvent, and can also include nanoparticles, microparticles and other particles made up of many molecules.

In various embodiments, the microneedle molding process includes one or more of the following steps before, during and/or after any or all of the mold filling steps: application of vibration, ultrasound, pressure, vacuum, an electromagnetic field, and centrifugation.

In one embodiment, precipitation of the active is controlled to occur in the microneedle and not in the funnel portion. By keeping the active in solution when the solution is still in the funnel will result in less active depositing onto the side walls of the funnel. To do this, the molds need to be filled with a solution that is not saturated with active. The solution should approach saturation as it dries to the point of only occupying the volume of the microneedle cavities. At this point the active will fall out of solution and migrate further into the microneedle cavities.

A variety of methods may be used to fill the molds. Examples include blanketing the entire area of the microneedle patch and/or filling individual funnels directly.

The microneedle cavities within a mold are closed at their tips. If a solution is cast on top of the entire mold or funnel, etc. air will remain within the microneedle/funnel cavity. This air needs to be removed in order to fill the molds with material and correctly replicate the microneedles. A variety of methods can be used to remove this air, including, but not limited to; 1) filling with solution under vacuum (i.e., no air is in the microneedle/funnel cavities to begin with), 2) applying vacuum after depositing the solution, which will cause the entrapped air to expand and rise up through and out of the solution, 3) applying a pressure gradient across a mold that is permeable to air (e.g., vacuum from the underside of the mold, pressure to the top side of the mold, or both) so that the air is expelled through the mold itself, 4) subjecting the molds to centrifugation to drive the solution into the molds, 5) using sonication or other physical methods from the bottom-side or top-side of the mold to expel air bubbles from the mold cavities, and/or 5) a combination of these methods.

Microneedle-by-microneedle filling is difficult using conventional microneedle molds due to the small target size (e.g., leads to misalignment and missing the individual microneedle reservoirs in the mold) and small volume that needs to be deposited (e.g., extremely small deposition volumes will lead to increased variation in the volume deposited). This becomes increasingly difficult in high-volume manufacturing. However, funnel-to-funnel (i.e., depositing filling materials into individual funnel mold cavities) and 'blanket' filling (i.e., covering areas of the mold surface that include multiple individual microneedle/funnel mold cavities) is much easier because the target area can be many times larger than the opening area of an individual microneedle cavity. With funnel-to-funnel filling, the fill volume (i.e., volume of microneedles and funnels) and targeted area (i.e., area of funnel-base interface) advantageously are many times larger than the fill volume and target area of a microneedle alone, so this can greatly reduce variation in the volume deposited (e.g., 5 nl±1 nl is 5 nl±20% and 100 nl±1 nl is 100 nl±1%—a 20-fold difference in the absolute variation in this scenario) and drop-to-target misalignments. With blanket filling, the entire area is covered with solution thereby further reducing the volume and positional constraints. The volume deposited via the blanketing method can be less than, equal to, or greater than the combined volume of the microneedles and funnels. Any excess solution is removed (e.g., wiped, air purged) once the microneedle and funnel cavities are filled.

The volume of solution deposited into the microneedle molds may be controlled by the volume of the cavities within a mold (i.e., completely fill cavity with solution and then clean surface) or the filler (i.e., dispense or load controlled volume, mass, etc.). For microneedle arrays produced by multiple filling steps, these volume control methods may both be used. For example, the solution containing the active is blanket coated over the entire surface, the microneedle and funnel cavities are filled, the solution is cleaned from the surface of the mold, the solution is dried, a second solution is deposited in a controlled amount by a filler, the second solution is dried, etc.

When filling a microneedle mold that does not have funnels, the amount of an active deposited in the microneedle is equal to the volume of the microneedle mold cavity multiplied by the concentration of the active in the filling solution. Increasing the amount of active in the microneedle can be achieved by increasing the concentration of the active in the filling solution. This will be limited by solubility, suspendability and other factors. Increasing the amount of active in the microneedle can be achieved by increasing microneedle mold cavity volume. This will be limited by how large the microneedle can be and still achieve its intended function, e.g., insertion into skin or other tissue, painless application etc. The addition of a funnel to the microneedle mold design effectively advantageously increases the volume of the microneedle mold during filling without changing the volume of the microneedle itself during use. This is because the microneedle and funnel portions of the mold can be filled together and, due to manufacturing process design, the materials dissolved, suspended or otherwise associated with the filling solution can be preferentially deposited in the microneedle portion of the mold upon drying. However, when the microneedle patch is applied to the skin or other tissue, only the microneedle portion substantially penetrates into the skin, whereas the funnel portion does not substantially penetrate into the skin, making it effectively part of the base portion of the patch.

Accordingly, microneedle arrays are provided herein that contain an amount of active in the microneedles (termed quantity A) (and/or administer an amount of active from the microneedle, termed quantity A') that is greater than the total volume of microneedles in the patch multiplied by the average concentration of the active in the filling solution during each of the one or more fillings employed during manufacturing multiplied by the number of fillings employed during manufacturing (termed quantity B). Conventional microneedle mold filling (without funnels) cannot achieve this amount of active (i.e., typically A or A'≤B). The use of funnels enables us to achieve this amount of active (A or A'≥B). For example, A or A'≥1.5 B; or A or A'≥2 B; or A or A'≥3 B; or A or A'≥5 B.

During blanket filling or other methods that do not place filling solution exclusively in mold cavities, there can be loss of filling solution left on the mold surface. During methods that intend to place filling solution exclusively in mold cavities, there can be loss of filling solution on the mold surface because of inaccuracies in the filling process that do not successfully place filling solution exclusively in mold cavities. Having larger areas at the top of the mold cavities makes exclusively filling the mold cavities easier to do, because deposition methods will be able to more easily selectively deposit material in mold cavities that have larger openings. The use of funnels allows that mold cavity opening to be larger than the base of the microneedle. The base of the microneedle using conventional molds that do not include funnels is at the interface of the microneedle and the base of the mold. Thus, the base of the microneedle defines the size of the opening of the mold cavity. In contrast, the base of the microneedle using molds that include funnels is at the interface of the microneedle and the funnel, and the size of the opening of the mold cavity is at the interface of the funnel and the base of the mold. In this way, the size of the base of the microneedle and the size of the opening of the mold cavity can be at least partially dissociated. The geometries of these interfaces are described above in the section of geometry of microneedles and of molds.

In another embodiment, methods of making microneedle arrays are provided in which one or more of the filling solution(s) are applied to the mold such that substantially all of the filling solution is deposited in the mold cavities (i.e., within the funnel and microneedle portions of the mold) and almost none of the filling solution is deposited on the mold surface. The ability to have this selective deposition of the filling solution is enabled by having large mold cavity openings enabled by the use of funnels. More specifically, the inclusion of a funnel portion enables methods in which the ratio of the amount of one or more actives deposited in the mold cavities (i.e., within the funnel and microneedle portions of the mold) to the amount deposited onto the mold is ≥80%, more preferably ≥90%, more preferably ≥95%, more preferably ≥98%, more preferably ≥99%. In embodiments, the ratio of the amount of one or more actives within the funnel and microneedle portions of the patch to the amount found in the whole patch (i.e., including the backing) is ≥80%, more preferably ≥90%, more preferably ≥95%, more preferably ≥98%, more preferably ≥99%.

In embodiments, methods are provided to make microneedle patches in which each microneedle cavity is filled by separate filling-solution droplets (in parallel and/or in series) and where the droplets have a volume larger than the volume of the microneedle (i.e., the microneedle portion of the mold). The absolute volumes of the filling solution droplets may be the same as the volumes identified above for the combined volumes of the microneedle and funnel portions of microneedle patches and molds. Ratios of the microneedle volume (i.e., volume of the microneedle in the microneedle patch or volume of the microneedle portion of the mold) to the droplet volume may be equal to the ratio of the microneedle volume to the sum of the microneedle and funnel volumes (or the sum of the microneedle and funnel portions of the mold) described above. More specifically, ratios of droplet volume to microneedle volume may be >1, more preferably ≥1.5, more preferably ≥2, more preferably ≥3, more preferably ≥5. The "droplet volume" may be considered to be the sum of the volume of multiple droplets applied to the same mold cavity before substantial drying occurs, since it is likely that the fill of each mold cavity will not be with a single drop but with multiple drops.

Other filling methods may be used to provide selective filling within a patch and within a needle including: applying localized and selective pressure gradients to only fill the desired locations, varying the surface properties (e.g., surface tension, specific and non-specific binding site) of the mold in order to selectively fill the desired locations, in the case of filling with microchannels, the microchannels could be divided only to cover and fill the desired portions of a patch or multiple solutions could be used that are either non-miscible or miscible, but under low Reynolds Number flow (little or no mixing) to fill only the desired locations.

In one embodiment, a fluid handling/dispensing technology/system known in the art to be capable of depositing solutions onto the molds is used. Some are suited for 'blanket' coating (regional or full patch), targeted deposition, or both. A few examples of fluid handling/dispensing systems are: syringe or other pumps coupled with dispensing heads (Tecan/Cavro, Gilson, Hamilton), automated pipetting systems (Tecan, Biotek, Eppendorf), screen printing or other mask and clean type systems, slot coating or similar systems, inkjet printing systems (MicroFab), pin or capillary array dispensing technologies, active capillary systems (Nanodrop by Innovadyne), aerosol or spraying based systems, dipping, brushing, stamping, surface chemistry controlled deposition (PRINT—Particle Replication In Nonwetting Templates), acoustic based systems (Picoliter, Inc.), and any combination of these deposition technologies (e.g., BioJet by BioDot, a syringe pump—inkjet hybrid). The filling heads may be automated and move, the molds may move, or both may move, in order to deposit the solutions in the desired locations. This may be in the form of single-cavity molds, multi-cavity mold plates, or on a continuous reel-to-reel process. We disclose methods of filling microneedle molds in which all the microneedle cavities and funnels are filling at substantially the same time or in which different microneedle cavities and funnels are filled at different times. This can be accomplished using droplets of filling solution applied selectively to individual or subsets of microneedle cavities and funnels. This can be accomplished by "blanket" filling of selected regions of the mold.

In one embodiment, vacuum filling is used. Vacuum can be applied before depositing the solution onto the molds. This removes the majority of the air prior to filling the mold. Also, vacuum can be applied after depositing the solution onto the mold. This removes the air from the cavities by causing it to expand and rise up through the deposited solution and out of the mold. The vacuum can be applied to the whole mold or to selected regions of the mold, to flow through a gas permeable/porous mold or both. such as the topside or the underside or a subset of microneedle cavities and funnels, such as to selectively fill those microneedle cavities and molds with filling solution(s).

Figure 18:
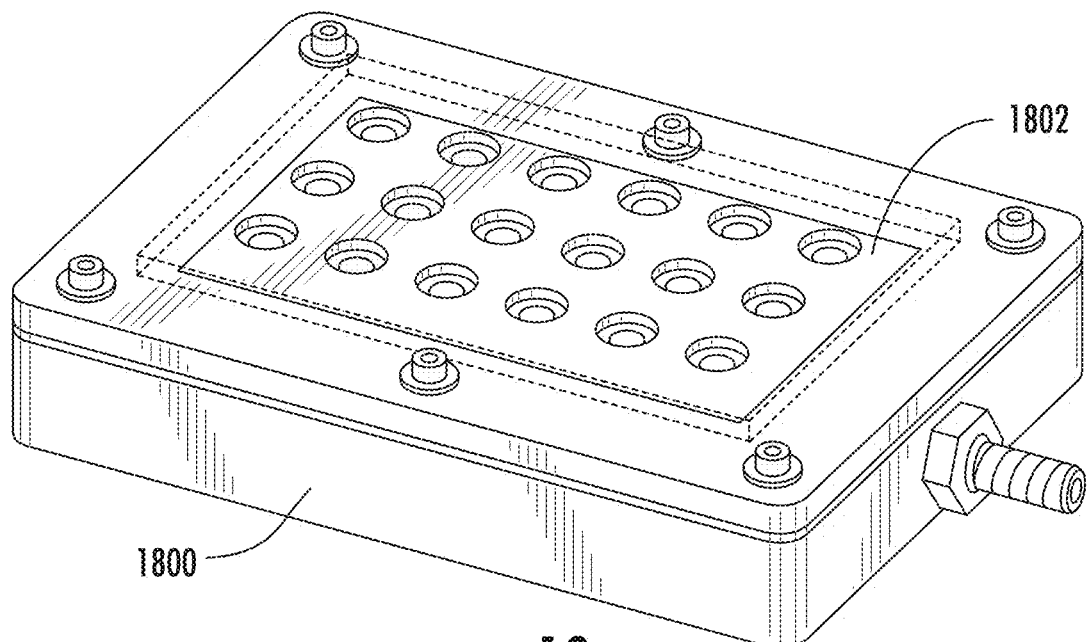

In a particularly preferred embodiment, filling of molds is carried out by applying vacuum through a gas permeable mold. For example, the vacuum can be applied exclusively to the underside of the mold, so as to create a pressure differential across the mold (e.g., between the upper, open surface of the mold and the opposed lower closed surface of the mold). One example of a vacuum apparatus for implementing such vacuum filling is shown in FIG. 18, which shows vacuum plate 1800 having an upper surface on which a gas-permeable mold 1802 is placed in mating on its bottom side with a gas permeable/porous surface of the vacuum plate, thereby pulling the vacuum through the mold. The upper surface of the mold has an array of openings into microneedle shaped cavities. By using a mold that has discrete pores/openings or a mold that is solid, but highly permeable to gases (air, nitrogen, etc.), the microneedle/funnel reservoirs can be filled simply by covering the opening of a funnel, multiple funnels, or an entire mold with the solution and then applying vacuum from the underside of the mold. This pulls the air out through the mold and creates a pressure gradient to pull the solution into the cavities. See Example 8. Such a process advantageously can eliminate a transfer step for placing the entire mold into a vacuum chamber.

The mold used in this process can be made of any suitable gas permeable material, which is substantially impermeable to liquids. It preferably is a non-porous material, having no interconnected pores in which solids can become trapped. In a preferred embodiment, the mold is made of an elastomeric material such as silicone, e.g., polydimethylsiloxane.

It has been discovered that the time to remove the air and fill the mold with solution is not strongly influenced by the solution viscosity, so it works well with both low viscosity and high viscosity solutions. The fill time may for example be two to four minutes using this method. The vacuum process advantageously is highly scalable because it can be done in parallel.

In another particularly preferred embodiment, which optionally may be used in combination with the preceding vacuum filling embodiment, the filling of a gas permeable mold is carried out by applying an over pressure to the solution at the upper side (the cavity opening side of the mold). By injecting the solution into the mold or mold cavity with pressure, the air can be forced out through the mold itself, if the mold has discrete pores/voids or is a solid mold made of a material (e.g., silicone/PDMS) that is permeable or highly permeable to gases, but not very permeable to liquids. For example, applying modest amounts of pressure (65 psi, i.e., pressure differential of ~50 psi) to the solution has been shown to force the solution down into the cavities and air out through the PDMS mold or into the solution itself within 20 seconds. The time to fill the molds with solution is not strongly influenced by viscosity. See Example 9. This can be done by pressurizing a chamber above the mold. This chamber can be pressurized by a gas directly, or via a gas moving a barrier material (e.g., a piston or membrane) to apply pressure directly to the solution. The pressure may also be applied similar to a traditional injection molding type process. The pressure may be applied mechanically by pressing on a movable barrier (e.g., a piston or membrane) or directly on the solution itself in the form of a plate or roller.

Therefore, in certain embodiments, filling of molds is performed by applying pressure to the topside of a mold, which may consist of applying pressure exclusively to the topside of the mold. In other embodiments, filling of molds is performed by applying vacuum exclusively to the underside of the mold. In other embodiments, filling of molds is performed by a combination of applying pressure to the topside of a mold and applying vacuum to the underside of the mold. Pressure gradients applied may be between 1 and 1000 psi and preferably between 10 and 100 psi.

The terms "pressure differential" and "pressure gradient" may be used interchangeably herein. The terms refer to the a difference in pressure used to create a driving force through the at least part of a thickness of a mold, by the creation of a sub- or super-atmospheric pressure on an upper or lower side of the mold, such as for example by the use of a pump. This "pressure differential" does not include intrinsic small differences in atmospheric pressure or fluid pressure, caused by gravity, by virtue of the upper surface of the mold being positioned above the lower surface of the mold or a head of fluid (e.g., casting solution) being on top of the mold.

In one embodiment, direct droplet deposition is used to carry out the filling of the molds. By depositing small drops via inkjetting or other technology, aerosols, or narrow fluid streams, the microneedle and funnels can be filled directly without the need for external pressure or vacuum to be supplied, since they are able to fill the microneedle/funnel cavity from the bottom up (i.e., microneedle tip up through the funnel-base interface and beyond). The droplets or streams are on the size scale that is significantly less than the size scale of the microneedle/funnel cavities (i.e., drop/stream width to cavity width) all on a size scale that is significantly less than size of the mold cavities). It may be difficult to administer droplets to microneedle molds without funnels, because droplets from deposition apparati may be larger than the microneedle-base interface width. This is an advantage of using funnels, in which the width of the funnel-base interface is larger than the width of the microneedle-funnel interface. The use of the funnel allows larger droplets to be used. Therefore, in one embodiment, the process of manufacture includes filling molds with droplets that have a width that is smaller than the width of the funnel-mold interface, and possibly larger than the width of the funnel-microneedle interface, or that have a width that is smaller than the width of the funnel-microneedle interface.

In another embodiment, a method for filling includes placing discrete capping structures, thin film microcapillaries, and/or semi-continuous surface microchannels onto the molds, filling them with solution, and then filling the microneedle/funnel cavities by using a pressure gradient. The pressure gradient can be supplied as already described (i.e., applying vacuum from the underside of the mold and/or pressurizing the solution within the cap/channel). See Example 6. Solution can flow through these structures by other mechanism as well, such as capillary flow, electroosmosis and/or other mechanisms known in the art of microfluidics. In such embodiments, filling of the microneedle mold cavities uses a filling solution applied from the side of the mold that flows in a direction substantially perpendicular to the central axis of the cavity. This contrasts with conventional filling methods that fill microneedle mold cavities with filling solutions applied from above the molds, flowing (through air) in a direction substantially parallel to the central axis of the cavity.

In one embodiment, a custom filling head is brought into contact and makes a fluidic seal with the open side of the mold whereby a pressure gradient is added to drive and/or pull the solution into the mold. The filling head contains a solution reservoir that may contain a volume that is equal to, greater than, and preferable much greater than the microneedle/funnel mold cavities to be filled. The reservoir may also be refillable in-process, refillable outside of the process (e.g., remove it, fill it, reinstall it), or disposable, where it or it and the filling head is (are) replaced with a new unit that is full. The filling head may be a tube with a thin and/or rounded edge, or may have and o-ring, gasket, or other sealing material so it can make sufficient contact with the mold to make a fluid seal. The filling head may also have a porous material on its front face, where the porosity (pore size and number) and surface chemistry is controlled so that it does not dispense solution without an applied pressure gradient. The filling head may be slid to the next microneedle array(s) (e.g., keeping its fluidic seal, face seal) or the solution may be retracted and the filling head may be lifted off the mold and repositioned onto the next microneedle array(s). A filling system and method may utilize more than one filling head. The filling head may be an elongated slot or some other geometry other than tubular that is more suitable for depositing the solution onto many microneedle patch cavities simultaneously. In an embodiment, the face seal filling head beneficially removes excess solution from the face of the mold over the filled cavities.

Figure 27:
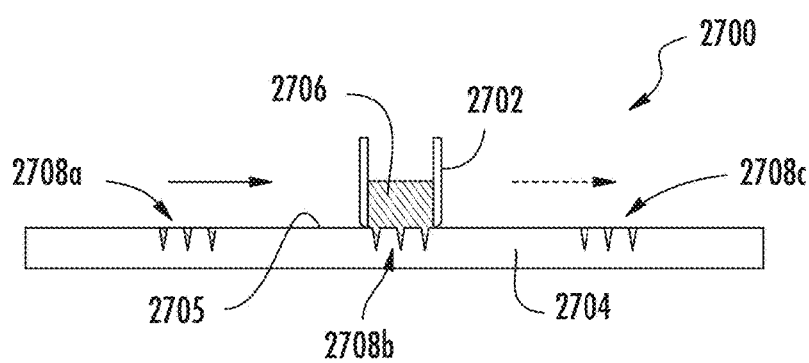

FIG. 27 illustrates one embodiment of a system and filling method which includes the use of a filling head. System 2700 includes a gas permeable mold 2704 having three microneedle cavity arrays 2708a, 2708b, and 2708c (shown with each array having three microneedle cavities) wherein each array has openings on upper surface 2705 of the mold 2704. A filling head 2702 contains filling material 2706 and mates against the upper surface 2705 of the mold 2704 and is shown in position filling microneedle cavity array 2708b. The horizontal arrows illustrate the movement of the filling head 2702 across the upper surface 2705 of the mold 2704 to sequentially fill the cavity arrays with filling material 2706, typically with aid of a pressure differential across mold (i.e., pressure assisted and/or vacuum assisted). Another way to expel air from the mold cavities and allow the deposited solution to enter is to apply physical energy to the mold to displace the air bubble up through or into the solution. For example, sonication may be applied from the bottom-side of the mold to expel the air from the cavities or it may be applied on the top-side of the mold and within the solution used to fill the cavities. Also, impact could be applied from the bottom-side of the mold to expel the air from the cavity. Or stretching an elastomeric mold may be used to expel the air. By stretching the elastic mold, the cavities can be closed down, thereby displacing the air, the solution can be applied, the mold is allowed to return to its original state, and the cavities fill with solution.

A sponge (e.g., foam, fabric, or other absorbent material) filling head may be used to fill the molds by pressing a saturated or partially saturated (with filling solution) filling head against the microneedle/funnel cavities. The filling head(s) may be pressed against the mold and held in place one time or many times. When the sponge containing the deposition solution is pressed against mold it is deformed and expels solution that is forced (e.g., by pressure) into the microneedle/funnel cavities, thereby filling and pushing out air from the cavities through the mold walls. After fill, the force is released, the sponge relaxes and then can be used to 'mop' or clean the surface of any residual solution. There can be more than one sponge filling head. The sponge filling head may also be in the form of a roller. The sponge filling heads may be replenished with solution in-process by dispensing solution onto them. Or a portion of the sponge may be in contact with a supply reservoir at all times so its solution saturation level remains relatively constant.

Drying

A number of drying and/or curing methods can be used throughout the manufacturing process. Heat may be applied in the form of a batch process, but it may be preferred to be integrated into a semi-batch or continuous process. Some of the drying methods, which harden the solution by removing the solvent via evaporation, include the application of: 1) heat—through convection, conduction (i.e., hot plate or heated surface), and/or radiation (heat lamp, IR or NIR light), 2) convection—dry, desiccated, sterile air or nitrogen blower, 3) vacuum—exposure to reduced pressure, 4) ambient drying, 5) desiccation, 6) lyophilization or freeze drying, 7) dielectric drying (e.g., rf or microwaves), 8) supercritical drying, and 7) a combination of one or more drying methods.

A number of the curing methods (hardening of the substance results from polymerization/cross-linking or reversible polymerization/cross-linking of polymer chains) are brought about by electron beams, heat, or chemical additives/reactions. Curing triggers may include time ultraviolet radiation (e.g., UV light), pressure, heat, etc.

In an embodiment, the aqueous solution may be dried at ambient temperature for a period from about 30 minutes to about one week to form the dry solid microneedles (e.g., from about 45 minutes to about one week, from about one hour to about one week, from about one hour to about one day, etc.). In one embodiment, the aqueous solution may be vacuum-dried using a backside vacuum for a period from about 3 minutes to about 6 hours, from about 3 minutes to about 3 hours, from about 3 minutes to about 1 hour, or from about 3 minutes to about 30 minutes. Although various temperatures and humidity levels can be employed to dry the aqueous solution, the formulations preferably are dried at temperature from 1° C. to 60° C. (e.g., from 15° C. to about 45° C., from about 25° C. to about 45° C., or at about ambient temperature) and 0 to 40%, 0 to 20%, 0 to 10% or at ambient relative humidity.

As used herein, the term "drying," "dried, or "dry" as it refers to the material in the mold (e.g., the matrix material and/or the substance of interest) refers to the material becoming at least partially solidified. In embodiments, the microneedles may be removed from the mold before being fully dried. In one embodiment, the microneedles are removed from the mold after the microneedles are dried to be an operational state. However, in a preferred embodiment, the microneedles are removed from the mold when the microneedles are in a rubbery state but strong enough to be pulled or peeled out of the mold. This has been found to improve demolding without microneedle breakage. As used herein, the term "operational state" means that the microneedles are sufficiently rigid to be used for their intended purpose, e.g., to penetrate skin. As used herein the term "rubbery state" means that the microneedles are not in an operational state, as they are too soft and flexible to penetrate their intended target tissue, e.g., skin. For example, a microneedle, such as one comprised of a bulk/matrix material including polyvinyl alcohol and a sugar, would, when undergoing a drying process, enter a rubbery state, as its moisture content is reduced, before entering the operational state.

De-Molding the Cast Product

The microneedle patches can be removed from the molds using a variety of methods. Non-limiting examples include 1) affixing an adhesive pad or backing to the backside of the microneedle array and demolding and assembled microneedle patch from the mold, 2) removing the microneedle array from the mold and affixing it to the adhesive pad or backing using pick-n-place automation techniques (picked up by suction cup or small grippers), 3) ejecting from the molds using ejector pin or other mechanical technique that is similar to traditional injection molding processes.

Additional Process Steps

In embodiments, a microneedle patch is composed of a first portion of the patch that is made using a mold-filling method and a second portion of the patch that is not made using the same mold-filling method. In particular, the second portion of the patch may be made before the first portion of the patch is made. The second portion of the patch may be combined with the first portion of the patch at some point during or after the mold-filling process used to make the first portion of the patch. The first portion of the patch could be the microneedle, funnel and base, and contain one or more actives. The second portion of the patch could be a backing that is affixed to the topside of the molded base.

The microneedle patches may be inspected prior to packaging to ensure that they meet their specifications. The machine vision industry has developed a number of technologies that can be adapted for this purpose. A number of inline and non-contact automated inspection systems (digital inspection scopes (Keyence), chromatic confocal imaging (Nanovea), and reflection based systems) can be used.

The patches that meet their specification are then packaged. In a preferred embodiment, the package protects the microneedle patch and its contents (i.e., active(s)) from mechanical damage, moisture, light, oxygen, and/or contamination (e.g., particulate, microbial). A single microneedle patch may be affixed to a cap or multiple microneedle patches may be affixed to a tray. The cap or tray may be made formed from plastic, metal (aluminum), metallized plastic, or other material. Examples of such microneedle patch caps and trays are described in PCT Patent Application Publication No. WO/2015/048777 to Georgia Tech Research Corporation.

4. METHODS OF USING THE MICRONEEDLE ARRAYS

The microneedle arrays and patches provided herein may be self-administered or administered by another individual (e.g., a parent, guardian, minimally trained healthcare worker, expertly trained healthcare worker, and/or others). Unlike prior art microneedle systems, the microneedle patches provided herein may be directly handled and administered by the person applying the patch without requiring use of an applicator to apply the required force/pressure, thereby allowing for a very simple, low-profile (i.e., thin and patch-like) microneedle patch (e.g., the total patch thickness, including any application aids, does not exceed 2 cm, more preferably 1.5 cm, more preferably 1 cm, and more preferably 0.5 cm).

Thus, embodiments provided herein further include a simple and effective method of administering a substance of interest with a microneedle patch. The method may include identifying an application site and, preferably, sanitizing the area prior to application of the microneedle patch (e.g., using an alcohol wipe). If needed, the application site may be allowed to dry before application of the microneedle patch. The patch then is applied to the patient's skin/tissue and manually pressed into the patient's skin/tissue (e.g., using the thumb or finger) by applying a sufficient pressure to insert the one or more microneedles into the patient's skin/tissue. After administration is complete, the patch may be removed from the patient's skin/tissue by manually grasping a tab portion (e.g., between the thumb and finger), peeling the patch off the patient's skin/tissue, and discarding the patch.

In embodiments, the microneedle patches described herein are used to deliver one or more substances of interest (e.g., vaccines, therapeutics, vitamins) into the body, tissue, cells, and/or organ. In one embodiment, the microneedles are used to deliver the active into skin by inserting the microneedles across the stratum corneum (outer 10 to 20 microns of skin that is the barrier to transdermal transport) and into the viable epidermis and dermis. The small size of the microneedles enables them to cause little to no pain and target the intradermal space. The intradermal space is highly vascularized and rich in immune cells and provides an attractive path to administer both vaccines and therapeutics. The microneedles are preferably dissolvable and once in the intradermal space they dissolve within the interstitial fluid and release the active into the skin. Once the microneedles are fully dissolved, which generally takes a few minutes (e.g., <20 minutes), the patch can be removed and discarded as non-sharps waste since the microneedles dissolve away. The microneedles can be altered to provide for more rapid release or quicker separation from the patch. They can also be formulated to release active over extended periods. Alternatively, the microneedles can be designed to rapidly separate from the patch, but then dissolve away slowly. A combination of these release features can be contained within a single microneedle patch to provide the desired release profile of the agent.

In one embodiment, a method is provided for administering a substance of interest to a patient, which includes providing one of the microneedle arrays described herein; and applying the microneedles of the array to a tissue surface of the patient, wherein the insertion of the microneedles of the array into the skin is done manually without the use of a separate or intrinsic applicator device. In this particular context, the term "applicator device" is a mechanical device that provides its own force, e.g., via a spring action or the like, which serves as the primary force to drive the microneedle array against the tissue surface, separate from any force the user may impart in holding the device and/or microneedles against the tissue surface.

5. Examples

The present invention may be further understood with reference to the following non-limiting examples.

Example 1: Fabrication of a Microneedle Array Mold

A laser-engineered funnel based polydimethylsiloxane (PDMS, Sylgard 184, Dow Corning, Midland, MI) microneedle array mold was prepared on the surface of 2.0-mm-thick PDMS sheet using a Universal Laser systems (VLS 3.50). The microneedle array mold included multiple cavities, wherein each cavity included a first cavity and a second cavity. The first cavity defined a primary funnel portion with 300-700 µm in height and 500-1000 µm in diameter at the widest point. The second cavity defined a conical microneedle with 600-900 µm in height, 250-300 µm in diameter at the widest point, and ~10 µm in tip radius.

Example 2: Fabrication of a Microneedle Array Molds

A polylactic acid (PLA) microneedle master structure was made by casting molten PLA pellets (L-PLA, 1.0 dL/g, Birmingham Polymer, Pelham, Ala.) onto the PDMS multi-cavity mold prepared in Example 1 under vacuum at −91 kPa for 1 h at 195° C. After which, PDMS multi-cavity mold replicates were then made by curing PDMS on top of the PLA master structure at 37° C. overnight.

Example 3: Fabrication of a Microneedle Array

A microneedle matrix material was prepared with polyvinyl alcohol (PVA) (MW 2000, ACROS Organics, Geel, Belgium) and sucrose (Sigma-Aldrich, St Louis, Mo.) at a 1:1 mass ratio. Eight grams of PVA was dispersed in 15 ml of DI water at 25° C. and then heated to 90° C. for 1 hour to solubilize to form a PVA solution. After which, 6.0 g of sucrose was added and mixed homogeneously with the PVA solution. The resulting mixture was then heated for 2 hours and then centrifuged at 2000×g for 30 minutes to remove air bubbles in the mixture to form the microneedle matrix material. The microneedle matrix material was then cooled to 4° C. before use.

A model drug solution was prepared with Sulforhodamine B (MW 559 Da, Molecular Probes Eugene, Oreg.), a water-soluble, red fluorescent dye with excitation/emission peaks of 565/586 nm, in deionized water. The model drug solution was then pipetted onto the top surface of a PDMS multi-cavity mold to cover all the cavities and then was vacuumed at room temperature to ~91 kPa for 3 minutes. After vacuuming, residual drug solution on the top surface of the PDMS multi-cavity mold was pipetted off and recycled for reuse. The PDMS multi-cavity mold was then dried under centrifugation at 3000×g at room temperature for 5 minutes. After which, dried Sulforhodamine B adherent to the top surface of the PDMS multi-cavity mold was removed by Scotch tape (3M, St. Paul, Minn.).

Approximately 200 µL of the microneedle matrix material was then applied to the top surface of the PDMS multi-cavity mold to cover all the cavities. After which, the PDMS multi-cavity mold was vacuumed at room temperature to −91 kPa for 3 minutes, and followed by centrifugation at 3000 X g at room temperature for 5 minutes to remove bubbles.

The PDMS multi-cavity mold, filled with Sulforhodamine B and the microneedle matrix material, was then freeze-dried in a lyophilizer (VirTis Wizerd 2.0 freeze dryer, Gardiner, N.Y.) for approximately 24 hours. The freeze-drying steps were programmed as follows: the mold was frozen to −40° C. for 1 hour, and then vacuumed at 2.67 Pa at −40° C. for 10 hours. While the pressure was kept constant (2.67 Pa), the temperature was gradually ramped up to 0° C. for 1 hour, 20° C. for 1 hour, and 25° C. for another 10 hours. After lyophilization, the resulting microneedle array was removed from the PDMS mold using a double-sided tape (444 Double-Sided Polyester Film Tape, 3M, St. Paul, Minn.). Various microneedle arrays were prepared as disclosed in this example. The structural parameters of each microneedle array are summarized in the table below.

| | Microneedle | | | Funnel Portion | | | | | |
|---|---|---|---|---|---|---|---|---|---|
| Microneedle Array | Height (μm) | Base diameter (μm) | Volume (nL) | Height (μm) | Top diameter (μm) | Base diameter (μm) | Base angle | Volume (nL) | Total volume (nL) |
| 1 | 700 | 300 | 16 | 300 | 300 | 1030 | 40° | 115 | 131 |
| 2 | 700 | 300 | 16 | 300 | 300 | 800 | 50° | 76 | 92 |
| 3 | 700 | 300 | 16 | 300 | 300 | 650 | 60° | 56 | 72 |
| 4 | 700 | 300 | 16 | 400 | 300 | 965 | 50° | 137 | 153 |
| 5 | 700 | 300 | 16 | 500 | 300 | 1150 | 50° | 230 | 246 |
| 6 | 600 | 300 | 14 | 650 | 300 | 1050 | 60° | 257 | 271 |
| 7 | 750 | 300 | 18 | 650 | 300 | 1050 | 60° | 257 | 275 |
| 8 | 900 | 300 | 21 | 650 | 300 | 1050 | 60° | 257 | 278 |

Figure 17:
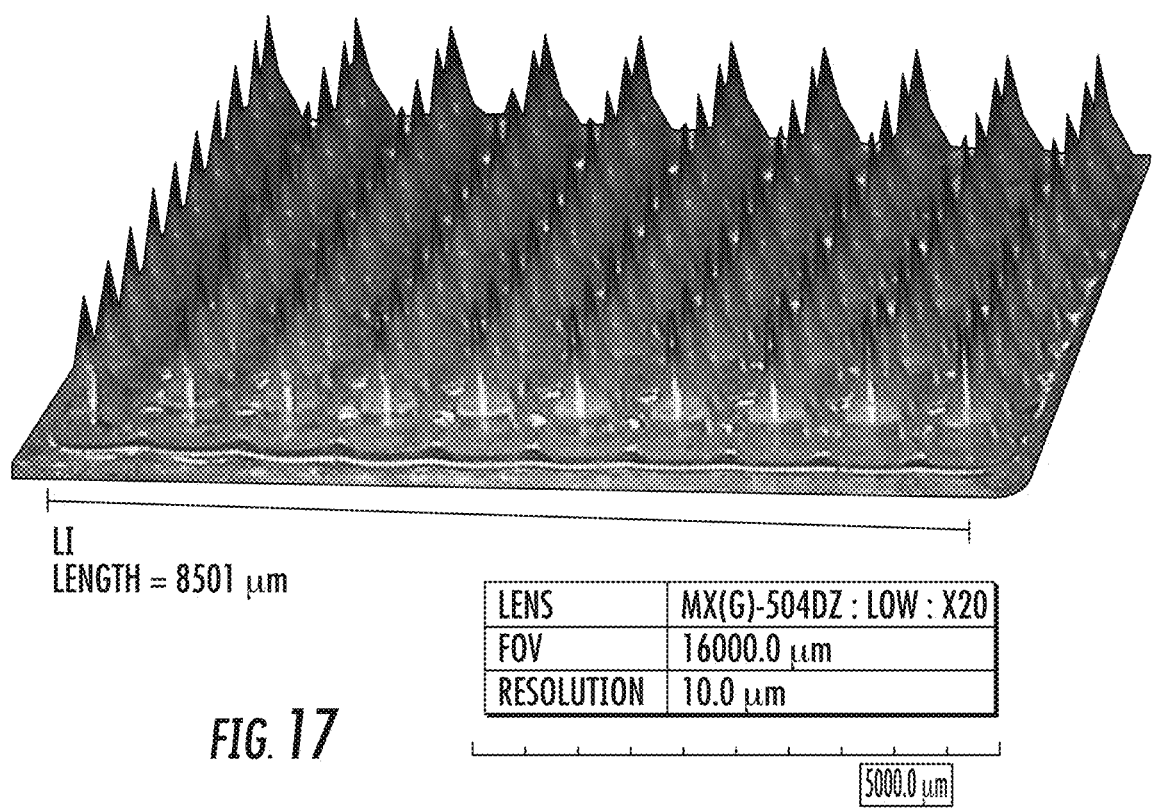
FIGS. 17 and 22-24 show some example embodiments of microneedle arrays and properties thereof as produced using some of the methods and systems described herein.

FIG. 17 is a microphotograph of a microneedle array prepared as disclosed in this example. As illustrated in FIG. 17, the model drug, Sulforhodamine B, is primarily located in the microneedles of the resulting microneedle array (i.e., more of the substance of interest is located in the microneedles than is located in the funnel portions).

Example 4: Drug Loading Capacity and Efficiency in a Microneedle Array

Figure 22:
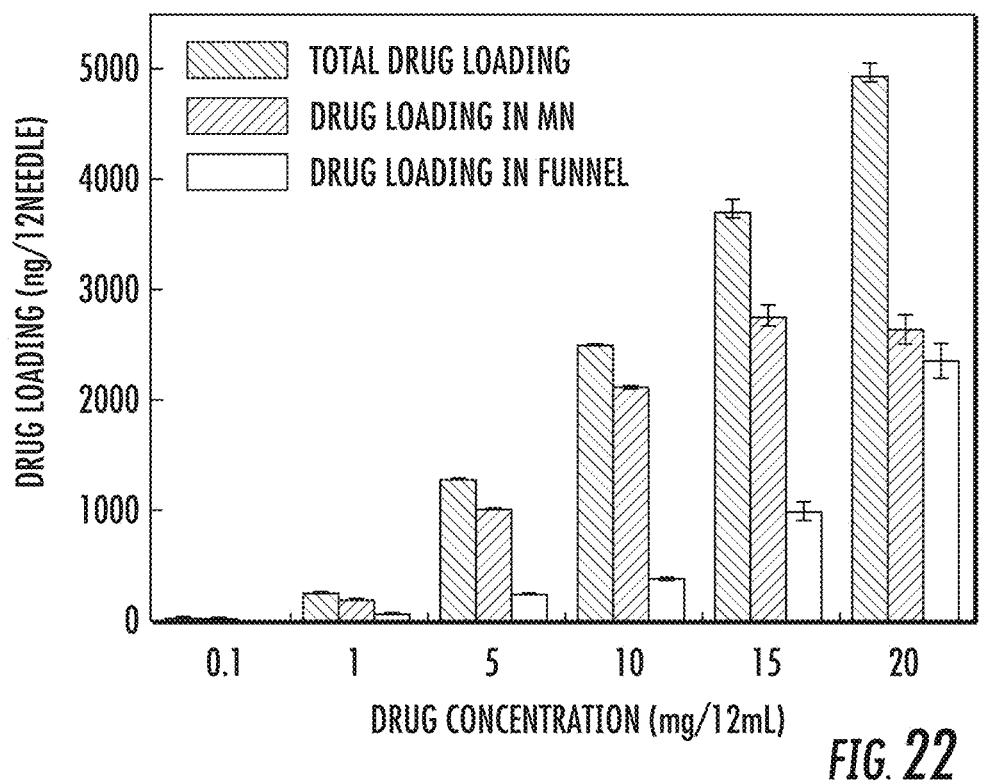
Figure 23:
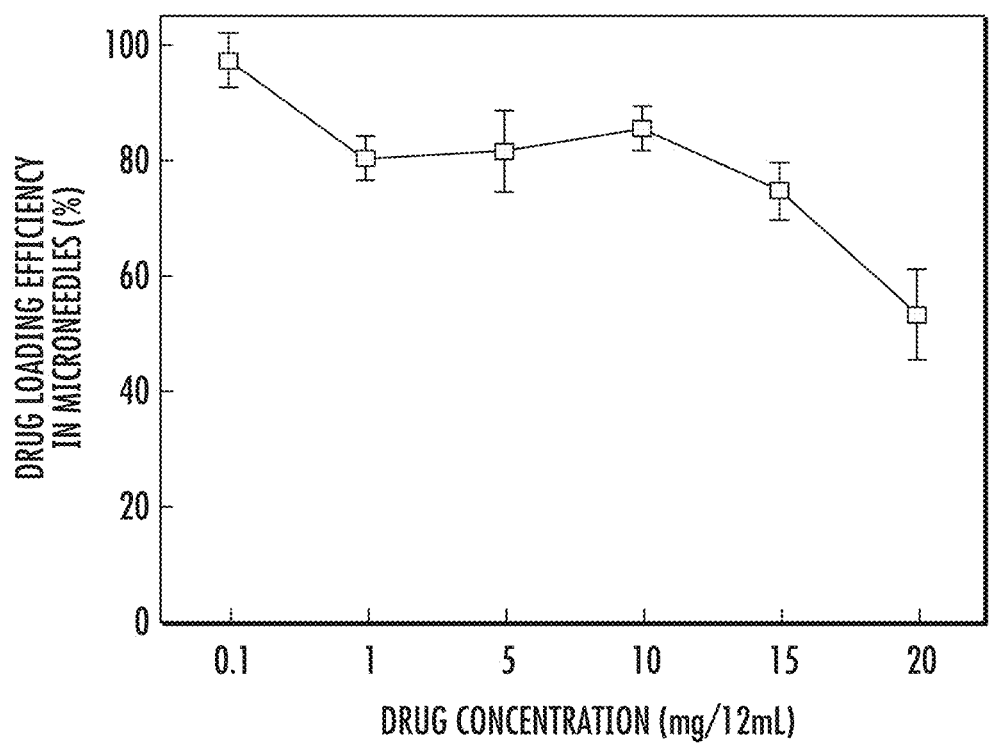

Six different microneedle arrays prepared as described in Example 2, each containing different drug concentrations (i.e., 0.1 mg/mL, 1.0 mg/mL, 5 mg/mL, 10 mg/mL, 15 mg/mL, and 20 mg/mL), were each dissolved in 10 mL of deionized water in separate containers for 1 hour at room temperature. Each dissolved microneedle array was then transferred into 96-well plates and measured by in a microplate reader (Multi-mode microplate synergy™ MX, Biotek) and analyzed with the Gen5™ software (Biotek). The basis for this experiment was the measurement of the emission/excitation spectrum of Sulforhodamine B, which was linearly proportional to the Sulforhodamine B concentration over a range of 0.001 m/mL to 1 m/mL. The average value of the signal for each microneedle array was used to determine the total amount of drug encapsulated in the microneedles and funnels ($A_{MN+F}$) of the microneedle array. The drug loading for each of the six microneedle arrays is shown in FIG. 22. The drug loading efficiency for each drug of the six microneedle arrays is depicted in FIG. 23.

Example 5: Evaluation of Drug Delivery Efficiency of a Microneedle Array

A study was conducted to measure the drug delivery efficiency of a microneedle array via in vitro testing using porcine cadaver skin (Pel-Freez, Rogers, Ariz.). The porcine cadaver skin, initially frozen, was first thawed to room temperature, and then shaved to remove all hair using a disposable razor (Dynarex, Orangeburg, N.Y.). The subcutaneous fat of the porcine cadaver skin subsequently was removed by a scalpel (Feather, Osaka, Japan).

Microneedle arrays prepared as described in Example 2, each with different sized cavities (primary funnel portions and microneedles containing Sulforhodamine B), were each manually inserted into the porcine cadaver skin for 5 seconds, 30 seconds, 1 minute, 2 minutes, 10 minutes, and 20 minutes. Each subset of microneedle arrays for each insertion time had 6 replicates. After each microneedle insertion, the microneedle array was microscopically imaged under the microscope (Olympus SZX16, Pittsburgh, Pa.) to determine whether the microneedles failed to insert (bent) or inserted, the amount of microneedle dissolved in the porcine cadaver skin, and whether part of the primary funnel portions dissolved in the porcine cadaver. The insertion site on the porcine cadaver skin was also observed using a microscope to determine whether the drug was delivered in the porcine cadaver. Adhesive tape (3M, St. Paul, Minn.) was then applied to the insertion site of the porcine cadaver skin to strip off the residual drug left on the skin surface.

After each insertion time, the tape and post insertion microneedle arrays were placed in separate containers of 10 mL of deionized water for 1 hour at room temperature to dissolve. Samples of the dissolved tape and dissolved microneedle arrays were then transferred into 96-well plates and measured by in a microplate reader (Multi-mode microplate synergy™ MX, Biotek) and analyzed with the Gen5™ software (Biotek). The basis for this experiment was the measurement of the emission/excitation spectrum of Sulforhodamine B, which was linearly proportional to the Sulforhodamine B concentration over a range of 0.001 m/mL to 1 m/mL. The average value of the signal for each dissolved tape sample was used to determine the total amount of drug left on the skin (AF) and the average value signal for each dissolved microneedle array was used to determine the total amount of drug encapsulated in the microneedles and funnels ($A_{MN+F}$) of the sampled microneedle array.

Figure 24:
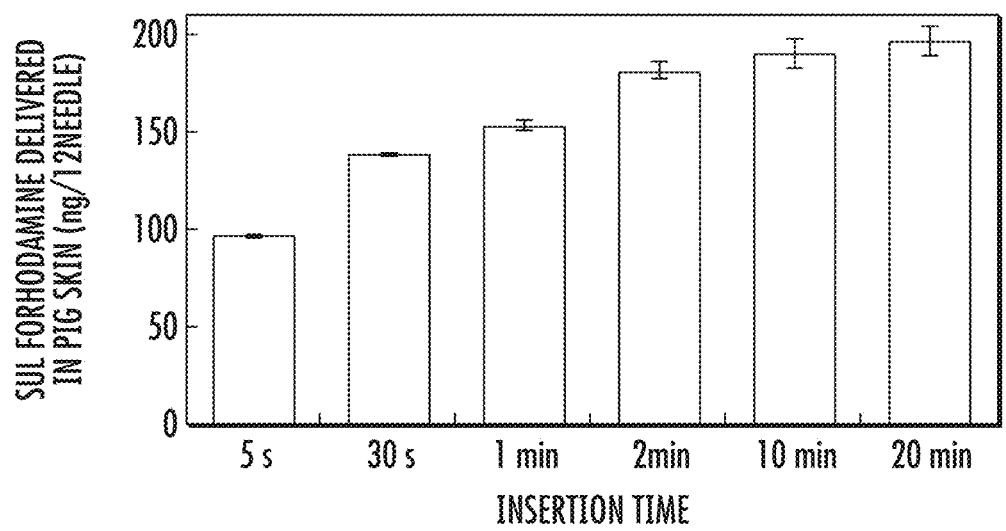

FIG. 24 depicts the amount of drug delivered to the skin for each insertion time using duplicate microneedle arrays containing 1.0 mg/mL of drug and having the following structural parameters: each cavity of the microneedle array, having a total volume of 275 nL, with a first cavity, defining a primary funnel portion with a height of 650 μm, a diameter of 1050 μm at its widest point, a volume of 257 nL, and a base angle of 60 degrees, and a second cavity, defining a microneedle with a height of 750 μm, a base diameter of 300

μm, and a volume of 18 nL. The amount of drug delivered into the skin ($A_{MN}$) was determined using the following equation:

$$A_{MN} = A_F - A_{MN+F}$$

wherein: $A_F$=amount of drug left on the skin and in the funnels
$A_{MN+F}$=total amount of drug contained in the microneedle array The drug delivery efficiency of each microneedle array was defined as:

$$\left(\frac{A_{MN}}{A_{MN+F}}\right) \times 100$$

wherein: $A_{MN}$=amount of drug delivered to the skin
$A_{MN+F}$=total amount of drug contained in the microneedle array

Example 6: Fabrication of a Microneedle Array Using Microchannel Structure

Figure 26:
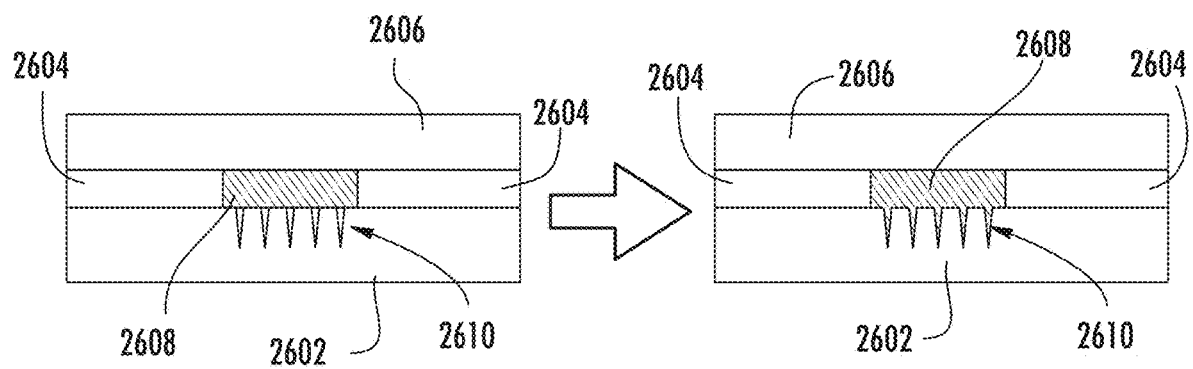

A microneedle array was formed in which mold filling was accomplished using a microchannel structure. FIG. 26 illustrates a cross-sectional view of a multi-cavity PDMS mold 2602 coupled to a thin film cell microchannel structure 2604 and closed on top by a thin polymer lid 2606. The microchannel structure 2604 was made with a thin adhesive layer and includes a microchannel 2608 connecting multiple microneedle cavity arrays spaced across the surface of the mold 2602. Only one microneedle cavity array 2610 is shown in FIG. 26. A model drug solution (sulforhodamine) was fed (via a syringe acting as a pump) through the channel 2608 (as shown in the left side of the figure) and a vacuum was applied for 10 minutes (27 in Hg vaccum) to the underside of mold 2602 (via a vacuum plate) causing the dye solution to be pulled into the cavities of the mold 2602 (as shown in the right side of the figure). The direction of flow of the dye solution through the channel is to be visualized and into/out of the page. Then, the dye solution remaining the channel 2608 was purged with air, forming the microneedles of the microneedle array.

The dye was allowed to dry, and then a fish gelatin and sucrose solution was cast over the mold. Vacuum was applied as before for 30 minutes and the microneedle arrays were allowed to dry and then were demolded. The patches were dissolved in dionized water and assayed for fluorescence. The results confirmed that the dye was loaded into the microneedles.

Example 7: Fabrication of a Microneedle Array

A microneedle multi-cavity mold was formed by 3D printing. Portions of the microneedle mold were 3D printed as tapered frustums (stepped sidewalls), each with a height of 1.0 mm and a diameter of 2.0 mm at the widest point, to form the funnel portion (positive).

The 3D printed structure was then cast with PDMS to create a mold of the funnel bases. A Universal Laser System (VLS 3.50) was then used to form the microneedle portion (negative) at the center of the funnel portion (negative) of the PDMS to produce a microneedle multi-cavity mold.

A model drug solution was then deposited onto the top surface of the resulting microneedle multi-cavity mold and then dried. A melted bulking polymer was then cast over the resulting microneedle multi-cavity mold and then cooled/ solidified. The resulting microneedle array was then removed from the microneedle cavity mold.

Example 8: Vacuum-Assisted Filling Through Mold

A vacuum plate for receiving a multi-cavity mold was designed, built, and evaluated. The vacuum plate and mold are shown in FIG. 18.

A mold made from polydimethylsiloxane (PDMS) (DC Sylgard 184) was used with the vacuum plate. The mold was 2 mm thick. Solutions of various viscosities were prepared and applied as a thin layer on the top surface of the mold. The solutions were water with 0.4% dye, a 40 wt % polyvinylpyrrolidone (PVP) solution, a 60 wt % PVP solution, and a solution of soldium carboxymethyl cellulose (CMC) and trehalose (1:1) (25% solids). A vacuum pressure of −13.8 psi was applied to the lower side of the mold for various periods of time. Whether microneedle cavity filling was achieved was then assessed.

The results are shown in the table below, and generally show that microneedle molds can be filled within 3 minutes by applying vacuum through the underside of the mold and that the time to remove the air and fill the mold with solution was not strongly influenced by the solution viscosity over the range considered.

| Solution | Approximate Viscosity (cP) | Time (minutes) | Successful Fill? |
|---|---|---|---|
| Water/dye | 1 | 1 | No |
| Water/dye | 1 | 2 | No |
| Water/dye | 1 | 3 | Yes |
| 40% PVP | 100 | 3 | Yes |
| 60% PVP | 1000 | 3 | Yes |
| CMC: Trehalose | ∞ | 3 | Yes |

Example 9: Pressure-Assisted Filling Through Mold

A pressure assisted fill of a microneedle mold was evaluated. The mold was made from PDMS (DC Sylgard 184) and was 2 mm thick. Solutions of various viscosities were prepared and applied as a thin layer on the top surface of the mold. The solutions were water with 0.4% dye, a 40 wt % polyvinylpyrrolidone (PVP) solution, and a 60 wt % PVP solution. A pressure of 50 psi or 65 psi was applied to the upper side of the mold (for a pressure differential across the mold of 35 or 50 psi, given atmospheric pressure of ~15 psi) for various periods of time. Whether microneedle cavity filling was achieved was then assessed.

The results are shown in the table below, and generally show that by applying modest amounts of pressure to the solution, one is able to force the solution down into the cavities and to force the air out through the mold or into the solution itself within 20 secods. The results also show that the time to remove the air and fill the mold with solution was not strongly influenced by the solution viscosity under the conditions studied.

| Solution | Approximate Viscosity (cP) | ΔP (psi) | Time (seconds) | Successful Fill? |
|---|---|---|---|---|
| Water/dye | 1 | 35 | 20 | No |
| Water/dye | 1 | 35 | 30 | Yes |
| 40% PVP | 100 | 35 | 30 | Yes |
| 60% PVP | 1000 | 35 | 30 | Yes |

-continued

| Solution | Approximate Viscosity (cP) | ΔP (psi) | Time (seconds) | Successful Fill? |
|---|---|---|---|---|
| 40% PVP | 100 | 50 | 20 | Yes |
| 60% PVP | 1000 | 50 | 20 | Yes |

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

We claim:

1. A method for making microneedles, the method comprising:
   (a) providing a mold having an upper surface, an opposed lower surface, and an opening in the upper surface, wherein the opening leads to a first cavity proximal to the upper surface and to a second cavity below the first cavity, wherein the first cavity defines a primary funnel portion, and wherein the second cavity defines at least one microneedle;
   (b) filling at least the second cavity, via the opening in the mold, with a first material which comprises a substance of interest dissolved or suspended in a first liquid vehicle;
   (c) drying the first material in the mold to remove at least a portion of the first liquid vehicle to form at least a tip portion of a microneedle in the second cavity, wherein the tip portion comprises the substance of interest;
   (d) filling the first cavity, and the second cavity if any is unoccupied following steps (b) and (c), via the opening in the mold, with a second material which comprises a matrix material dissolved or suspended in a second liquid vehicle;
   (e) drying the second material in the mold to remove at least a portion of the second liquid vehicle to form (i) a primary funnel portion, and (ii) any portion of the at least one microneedle unformed following steps (b) and (c), wherein the primary funnel portion comprises the matrix material; and
   (f) removing from the mold the at least one microneedle together with the primary funnel portion connected thereto,
   wherein more of the substance of interest is located in the at least one microneedle than is located in the primary funnel portion.

2. The method of claim 1, wherein the mold is a two-part mold, in which a first part comprises the first cavity and a second part comprises the second cavity.

3. The method of claim 1, wherein the first material further comprises a matrix material, and/or wherein the second material does not comprise the substance of interest.

4. The method of claim 1, wherein the mold is non-porous and gas permeable.

5. The method of claim 1, wherein:
   the filling of step (b) and/or step (d) is conducted with a pressure differential applied between the upper and lower surfaces of the mold,
   the mold is gas permeable, and
   a sub-atmospheric pressure is applied at the lower surface of the mold, a super-atmospheric pressure is applied at the upper surface of the mold, or a sub-atmospheric pressure and a super-atmospheric pressure are applied at the lower and upper surfaces, respectively.

6. The method of claim 1, wherein the filling of step (b) and/or step (d) comprises the use of a filling head which comprises a sponge or a roller.

7. The method of claim 1, wherein the second cavity defines two or more microneedles extending from the primary funnel portion.

8. The method of claim 1, wherein the mold is elastomeric and step (f) comprises elastically deforming the mold to facilitate separation of the mold from the primary funnel portion and the at least one microneedle.

9. The method of claim 1, wherein the drying of step (e) is partial drying such that the at least one microneedle is in a rubbery state at the end of step (e).

10. The method of claim 9, further comprising, after step (f), drying the at least one microneedle to transform the at least one microneedle from a rubbery state to an operational state.

11. The method of claim 1, wherein the drying of step (e) is effective to place the at least one microneedle in an operational state.

12. The method of claim 1, wherein the at least one microneedle further comprises a secondary funnel portion extending from the at least one primary funnel.

13. A method for making an array of microneedles, the method comprising:
   (a) providing a non-porous and gas-permeable mold having an upper surface, an opposed lower surface, and a plurality of openings in the upper surface, wherein each opening leads to a cavity which defines a microneedle;
   (b) filling the cavities, via the openings, with a fluid material which comprises a substance of interest dissolved or suspended in a liquid vehicle;
   (c) drying the fluid material in the mold to remove at least a portion of the liquid vehicle and form a plurality of microneedles which comprise the substance of interest; and
   (d) removing the plurality of microneedles from the mold,
   wherein the filling of step (b) is conducted with a pressure differential applied between the upper and lower surfaces of the mold.

14. The method of claim 13, further comprising filling at least part of the cavities with a second fluid material which comprises a matrix material dissolved or suspended in a second liquid vehicle, wherein the matrix material forms a base substrate connected directly to the plurality of microneedles or to one or more funnel portions, which are, in turn, connected to the plurality of microneedles.

15. A method for making an array of microneedles, the method comprising:
   providing a two-part mold having a upper portion and a lower portion, the upper portion having an upper surface, an opposed lower surface, and an opening extending therethrough, the opening defining an upper cavity, the lower portion having an upper surface, an opposed lower surface, and an opening in the upper surface which is in fluid communication with the upper cavity and which leads to a lower cavity, the lower cavity defining a microneedle, wherein the upper portion and the lower portion are separably secured together;
   filling at least the lower cavity, via the opening in the upper portion, with a first material which comprises a substance of interest dissolved or suspended in a first liquid vehicle;
   drying the first material in the mold to remove at least a portion of the first liquid vehicle to form a microneedle which comprises the substance of interest; and removing the microneedle from the mold.

16. The method of claim 15, wherein the upper cavity serves as a funnel during the filling of the lower cavity, and wherein the upper portion of the mold is separated from the lower portion of the mold before the microneedle is removed from the mold.

17. The method of claim 15, further comprising:
filling at least the upper cavity with a second material which comprises a matrix material dissolved or suspended in a second liquid vehicle,
wherein the drying further includes drying the second material to remove at least a portion of the second liquid vehicle to form, from the matrix material, (i) a distal part of the microneedle, (ii) a primary funnel, (iii) one or more secondary funnels, (iv) a base substrate, (v) a combination of (i), (ii) and (iv), or (vi) a combination of (i) to (iv).

18. The method of claim 15, wherein the lower portion of the mold comprises an array of two or more lower cavities defining microneedles, and the upper cavity leads to the two or more cavities.

19. The method of claim 18, wherein the upper cavity defines a primary funnel portion and the drying step yields two or more microneedles extending from the primary funnel portion.

20. A method of administering a substance of interest to a patient, comprising:
providing an array of microneedles produced by the method of claim 13;
applying the array of microneedles to a tissue surface of the patient; and
inserting the microneedles of the array into the tissue surface.

* * * * *